United States Patent
Watson et al.

(10) Patent No.: US 6,566,072 B1
(45) Date of Patent: May 20, 2003

(54) MAMMAGLOBIN, A SECRETED MAMMARY-SPECIFIC BREAST CANCER PROTEIN

(75) Inventors: Mark A. Watson, St. Louis, MO (US); Timothy P. Fleming, St. Louis, MO (US)

(73) Assignee: Washington University, St. Louis, MO (US)

(*) Notice: Subject to any disclaimer, the term of this patent is extended or adjusted under 35 U.S.C. 154(b) by 0 days.

(21) Appl. No.: 09/162,622

(22) Filed: Sep. 29, 1998

Related U.S. Application Data

(63) Continuation-in-part of application No. 08/933,149, filed on Sep. 18, 1997, now Pat. No. 5,922,836, which is a continuation-in-part of application No. PCT/US96/08235, filed on May 31, 1996, and a continuation-in-part of application No. 08/455,896, filed on May 31, 1995, now Pat. No. 5,668,267.

(51) Int. Cl.$^7$ .............................................. G01N 33/53

(52) U.S. Cl. ........................................ 435/7.1; 435/4

(58) Field of Search ............................................. 435/7.1

(56) References Cited

U.S. PATENT DOCUMENTS

| | | | |
|---|---|---|---|
| 5,573,916 A | 11/1996 | Cheronis et al. | |
| 5,593,972 A | 1/1997 | Weiner et al. | |
| 5,668,267 A | 9/1997 | Watson et al. | |
| 5,922,836 A | * 7/1999 | Watson et al. | |

FOREIGN PATENT DOCUMENTS

| WO | WO96/38463 | 12/1996 |
|---|---|---|
| WO | 98/07753 | * 2/1998 |

OTHER PUBLICATIONS

Reiger et al (Glossary of Genetics and Cytogenetics, Classical and Molecular, 4th Ed., Springer–Verlag, Berlin), 1976.*
Alberts et al (Molecular Biology of the Cell, 3rd Ed., 1994, p. 465).*
Shantz and Pegg (Int. J. of Biochem and Cell Biol., 1999, 31:107–122).*
McClean and Hill (Eur. J. Cancer, 1993, 29A:2243–2248).*
Fu et al (EMBO J. 1996, 15:4329–4401).*
Tockman et al (Cancer Res. 1998 (Suppl), 52:2711s–2718s).*
Allerd et al., J. Nat'l Cancer Inst. 85:200–206 (1993).
Bagshawa, Adv. Pharmacol. 24:99–121 (1993).
Bjork et al., Partial Characterization and "Quantitation" of a Human Prostatic Estramustine–binding Protein, Cancer Res. 42:1935–1942 (1982).
Bjork et al., Expression and Partial Characterization of Estramustine–Binding Protein (EMBP) in Human Breast Cancer and Malignant Melanoma, Anticancer Res. 11:1173–7792 (1991).
Borras–Cuesta et al., Eur. J. Immunol. 17:1213–1215 (1987).
Cato et al., The Hormonal Regulation of Uteroglobin Gene Expression, Anticancer Res. 5:65:72 (1985).
Denton et al., Cancer Letters 70:143–150 (1993).
Falk et al., Nature 351:290–296 (1991).
Good et al., Science 235:1059–1062 (1987).
Hammer et al., J. Exp. Med. 176:1007 (1992).
Henderson et al., Science 255:1264–1266 (1992).
Hill et al., Nature 360:434 (1992).
LoBuglio and Saleh, Am. J. med. Sci. 304:214–224 (1992).
Maroulako et al, Proc. Nat. Acad. Sci. USA 91:11236–11240 (1994).
Miele et al., Uteroglobin: Structure, Molecular Biology, and New Perspectives on its Function as a Phospholipase $A_2$ Inhibitor, Endocrine Rev. 8:474–490 (1987).
Miele et al., Uteroglobin and Uteroglobin–like Proteins: the uteroglobin family of Proteins, J. Endocrinol. Invest. 17:679–92 (1994).
Panina–Bordignon et al., Eur. J. Immunol. 19:2237 (1989).
Parker et al., Organization and Expression of Prostatic Steroid Binding Protein Genes, J. Steroid Biochem 20:67–71 (1984).
Parker et al., J. Biol. Chem. 258:12–15 (1983).
Parker et al., Organization and Expression of Genes Encoding Prostatic Steroid Binding Protein, Ann. NY Acad. Sci. 438:115–124 (1984).
Peeters et al, Eur. J. Biochem., 115:115–121.
Peoples et al., Proc. Natl. Acad. Sci. 92:432–436 (1995).
Peri et al., Tissue–Specific expression of the Gene Coding for Human Clara Cell 10–kD Protein, a Phospholipase $A_2$–inhibitory Protein, J. Clin. Invest. 92:2099–2109 (1993).
Sandmoller et al., Oncogene 9:2805–2815 (1994).
Schoenfield et al., Cancer Res. 54:2986–2990 (1994).
Slamon et al., Sci. 244:707–712 (1989).
Taylor et al., Virology 187:321–328 (1991).
Thor et al., J. Nat'l Cancer Inst. 84:845–855 (1992).
Toso et al., Cancer Research 56:16–20 (1996).
Watson et al., Cancer Res. 56:860–865 (1996).

(List continued on next page.)

Primary Examiner—Susan Ungar
(74) Attorney, Agent, or Firm—Thompson Coburn LLP

(57) ABSTRACT

A purified and isolated DNA sequence and the encoded mammary-specific secreted protein, mammaglobin, are disclosed. Also disclosed are methods for detecting breast cancer based upon the overexpression and secretion of mammaglobin by breast cancer cells. The methods detect and/or quantitate the presence of mammaglobin or the mRNA encoding mammaglobin. Immunotherapy-based methods for treating a breast cancer patient with a mammaglobin-expressing tumor are also disclosed. The methods involve using mammaglobin antigens to induce a humoral and/or cell-mediated immune response against the tumor.

7 Claims, 15 Drawing Sheets

OTHER PUBLICATIONS

Watson et al., Structure and transcriptional regulation of the human mammaglobin gene, a breast cancer associated member of the uteroglobin gene family localized to Chromosome 11q13, *Oncogene* 16:817–824 (1998).

Watson et al., Isolation of Differentially Expressed Sequence Tags from Human Breast Cancer, *Cancer Res.* 54:4598–4602 (1994).

Becker et al.; "Identification of Mammaglobin B, a Novel Member of the Uteroglobin Gene Family"; *Genomics*, vol. 54, 1998, pp. 70–78.

Peri et al.; Tissue–specific Expression of the Gene Coding for Human Clara Cell 10–kD Protein, A Phospholipase $A_2$–inhibitory Protein; *The Journal of Clinical Investigation, Inc.*, vol. 92, Nov. 1993, pp. 2099–2109.

Sambrook et al.; "Purification of Antibodies"; *Molecular Cloning, A Laboratory Manual*, second edition, 1989, pp. 18. 11–18. 18.

Stryer, Lubert; *Biochemistry*, third edition, 1988, pp. 28–29.

* cited by examiner

|  | 9 | 18 | 27 | 36 | 45 | 54 |
|---|---|---|---|---|---|---|

5' GAC AGC GGC TTC CTT GAT CCT TGC CAC CCG CGA CTG AAC ACC GAC AGC AGC AGC

|  | 63 | 72 | 81 | 90 | 99 | 108 |
|---|---|---|---|---|---|---|

CTC ACC ATG AAG TTG CTG ATG GTC CTC ATG CTG GCG GCC CTC TCC CAG CAC TGC
        Met Lys Leu Leu Met Val Leu Met Leu Ala Ala Leu Ser Gln His Cys
         1                                            10

|  | 117 | 126 | 135 | 144 | 153 | 162 |
|---|---|---|---|---|---|---|

TAC GCA GGC TCT GGC TGC CCC TTA TTG GAG AAT GTG ATT TCC AAG ACA ATC AAT
Tyr Ala Gly Ser Gly Cys Pro Leu Leu Glu Asn Val Ile Ser Lys Thr Ile Asn
            20                                           30

|  | 171 | 180 | 189 | 198 | 207 | 216 |
|---|---|---|---|---|---|---|

CCA CAA GTG TCT AAG ACT GAA TAC AAA GAA CTT CTT CAA GAG TTC ATA GAC GAC
Pro Gln Val Ser Lys Thr Glu Tyr Lys Glu Leu Leu Gln Glu Phe Ile Asp Asp
               40                                          50

|  | 225 | 234 | 243 | 252 | 261 | 270 |
|---|---|---|---|---|---|---|

AAT GCC ACT ACA AAT GCC ATA GAT GAA TTG AAG GAA TGT TTT CTT AAC CAA ACG
Asn Ala Thr Thr Asn Ala Ile Asp Glu Leu Lys Glu Cys Phe Leu Asn Gln Thr
                            60                                         70

|  | 279 | 288 | 297 | 306 | 315 | 324 |
|---|---|---|---|---|---|---|

GAT GAA ACT CTG AGC AAT GTT GAG GTG TTT ATG CAA TTA ATA TAT GAC AGC AGT
Asp Glu Thr Leu Ser Asn Val Glu Val Phe Met Gln Leu Ile Tyr Asp Ser Ser
                                       80

|  | 333 | 342 | 351 | 360 | 369 | 378 |
|---|---|---|---|---|---|---|

CTT TGT GAT TTA TTT TAA CTT TCT GCA AGA CCT TTG GCT CAC AGA ACT GCA GGG
Leu Cys Asp Leu Phe ***
        90

|  | 387 | 396 | 405 | 414 | 423 | 432 |
|---|---|---|---|---|---|---|

TAT GGT GAG AAA CCA ACT ACG GAT TGC TGC AAA CCA CAC CTT CTC TTT CTT ATG

|  | 441 | 450 | 459 | 468 | 477 | 486 |
|---|---|---|---|---|---|---|

TCT TTT TAC TAC AAA CTA CAA GAC AAT TGT TGA AAC CTG CTA TAC ATG TTT ATT

495

TTA ATA AAT TGA TGG CA 3'

Figure 2

```
hCC10  -21  MKLAVTLTLVTLALCCSSASAEICPSFQRVIETLLMDTPSS-
hMaM    01  MKLLMVLMLAALSQHCY-A-GSGCPLLENVISKTINPQVSKT
rPSC3   01  MKLVFLFLVTIPICY-ASGSGCSILDEVRGTINSTVTLH hCC10   20  -YEAAMELFSPDQDMREAGAQLKKLVDTLPQK--PRESIKL
hMaM    41  EYKELLQEFIDDNATTNAIDELKECF---LNQTDETLSNVEVF
rPSC3   42  DVMKLVKPYVQDHFTEKAVKQFKQCF---LDQTDKTLENVGVM hCC10   61  MEKIAQSSICN
hMaM    82  MQLIYDSIFDLF
rPSC3   83  MEAIFNSESGQQPS
```

Figure 3

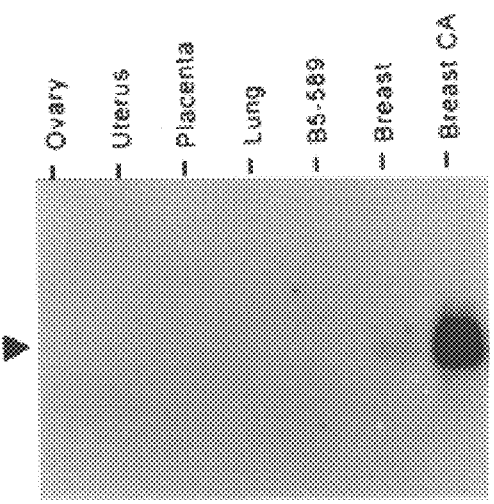
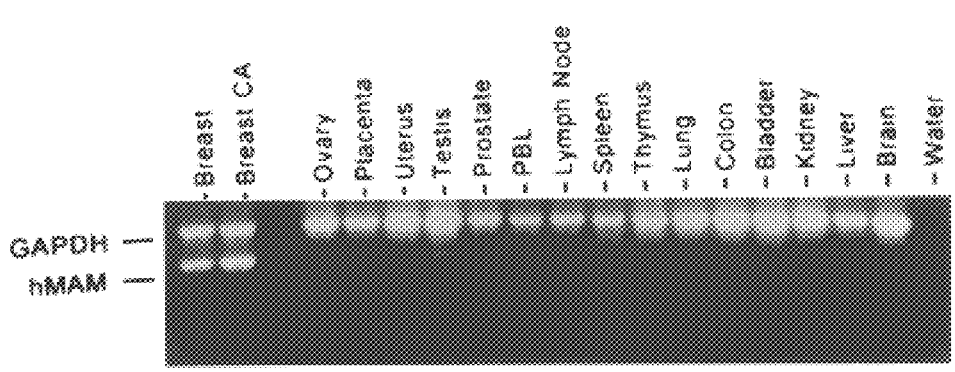
Figure 4A
Figure 4B

MAMMAGLOBIN, A SECRETED MAMMARY-SPECIFIC BREAST CANCER PROTEIN

RELATED APPLICATIONS

This is a continuation-in-part of application Ser. No. 08/933,149; filed on Sep. 18, 1997, now U.S. Pat. No. 5,922,836, which is a continuation-in-part of PCT/US96/08235, filed May 31, 1996 and a continuation-in-part of Ser. No. 08/455,896, filed May 31, 1995, now U.S. Pat. No. 5,668,267.

REFERENCE TO GOVERNMENT GRANTS

This invention was made with government support under Public Health Service Grants CA76227, CA76223-01 and CA68485. The government has certain rights in this invention.

BACKGROUND OF THE INVENTION (1) Field of the Invention

This invention relates generally to the field of breast cancer pathogenesis and, more particularly, to a cDNA sequence and encoded mammary-specific protein for use in detecting and treating breast cancer.

(2) Description of the Related Art

Breast cancer is one of the most common and potentially lethal of cancers. Although early diagnosis and treatment can reduce morbidity and mortality related to the disease, the positive predictive value of mammography has been estimated to be only about 25% (Hall et al., *N Engl J Med* 327:319–328, 1992). It would, therefore, be desirable to have a means for detecting the cancer earlier than the cancer can be detected using mammography and a genetic or biochemical marker might be able to provide such means to complement and increase the predictive value of mammography. (Hayes, *Hematol Oncol Clin N Am* 8:485, 1994).

The development of breast cancer is accompanied by a number of genetic changes (For review see Porter-Jordan, *Hematol Oncol Clin N Am* 8:73, 1994). Such changes include gross chromosomal alterations and loss of genetic markers (Devilee et al, *Biochim Biophys Acta* 1198:113, 1994; Callahan et al, *J Cell Biochem Suppl* 17:167, 1993). The progression of breast neoplasia has also been shown to result in qualitative and quantitative changes in expression of previously identified genes that encode growth factors and their receptors (Zajchowski et al., *Cancer Res* 48:7041, 1988), structural proteins (Trask et al., *Proc Natl Acad Sci* 87:2319, 1990), second messenger proteins (Ohuchi et al., *Cancer Res* 26:2511, 1986), and transcription factors (Harris, *Adv Cancer Res* 59:69:1992). These changes in gene expression could potentially form the basis for developing a breast cancer marker, although the precise role of these gene changes in the pathogenesis of breast carcinoma in patient biopsy samples is not well understood.

In addition to providing a genetic or biochemical marker for breast cancer for early detection of the disease, it would also be desirable to have a tumor marker that might provide an estimation of prognosis, a means for selection and evaluation of therapy and a means for the targeting of therapy. Although a number of tissue markers have been identified, none are sufficiently sensitive or tumor specific to be ideally suited for diagnosis or for screening the general population. (Id.) Thus, there remains a continuing need for a breast cancer marker such as a gene along with its expressed protein that can be used to specifically and selectively identify the appearance and pathogenic development of breast cancer in a patient, and that can be used in tumor-specific immunotherapy.

Using a modified differential display polymerase chain reaction technique to isolate differentially expressed sequence tags from mammary carcinoma, several sequence fragments were isolated that were uniquely expressed in neoplastic mammary epithelial tissue as compared to normal tissue controls (Watson and Fleming, *Cancer Res* 54:4598–4602, 1994). The discovery of one of these sequence tags identified as DEST002 has led to the discovery and isolation of the novel full length cDNA and encoded protein now referenced as mammaglobin. The cDNA and protein are both new.

SUMMARY OF THE INVENTION

Briefly, therefore, the present invention is directed to the identification of novel genes whose expression is increased in breast cancer and to the isolating of cDNA's from the mRNA's of these genes. Accordingly, applicants have succeeded in discovering a novel cDNA and the encoded mammary-specific secretory protein, mammaglobin. The cDNA is in purified and isolated form and comprises a nucleotide sequence identified as SEQ ID NO:15 and the encoded protein, mammaglobin, is in purified and isolated form and has an amino acid sequence identified as SEQ ID NO:2.

In a small-scale study described in U.S. Pat. No. 5,668,267, mammaglobin mRNA was overexpressed in 27% of stage I primary breast cancer tumors. The present application describes a larger survey of primary breast tumors of multiple grades and histological types in which mammaglobin protein was detected in about 80% of the tumors examined. These data suggest that dysregulation of the mammaglobin gene occurs early and frequently in breast cancer. The discovery of mammaglobin and its cDNA, therefore, provide the basis for the development of novel methods and compositions for the detection and treatment of breast neoplastic disease in humans and other mammals.

Thus, the present invention is directed to novel methods for detecting the presence of breast neoplasia cells in a sample. In one embodiment, a polynucleotide probe is used to detect the presence of mammaglobin mRNA in the sample. The method comprises the steps of: (a) contacting mRNA in the sample with a polynucleotide probe which specifically hybridizes to a mammaglobin mRNA comprising SEQ ID NO:15 or an allelic variant thereof, and (b) detecting a hybridization complex between the probe and the sample mRNA.

Another aspect of the present invention provides a kit for detecting the presence of breast neoplasia cells in a sample by hybridization. The kit comprises a polynucleotide probe which specifically hybridizes to a mammaglobin mRNA comprising SEQ ID NO:15 or an allelic variant thereof packaged in a container.

In another embodiment of the present invention, mammaglobin expression in a sample is determined by detecting the presence of cDNA that is reverse transcribed from mammaglobin mRNA in the sample. The method comprises the steps of: (a) producing a cDNA encoding mammaglobin from mRNA using the reverse transcription method in a sample obtained from a patient, (b) providing two primers for the polymerase chain reaction method which comprise oligomers that flank or lie within the cDNA encoding mammaglobin, and (c) amplifying the cDNA encoding mammaglobin by the polymerase chain reaction method.

Preferably, the two primers have nucleotide sequences encoding SEQ ID NO:4 and SEQ ID NO:16.

Another embodiment to the present invention provides a kit for detecting the presence of breast neoplasia cells in a sample by the polymerase chain reaction. The kit comprises two primers for the polymerase chain reaction method which comprise oligomers that flank or lie within a cDNA encoding mammaglobin packaged in a container. Preferably, the two primers have nucleotide sequences comprising SEQ ID NO:4 and SEQ ID NO:16.

In another embodiment of the present invention, the presence of mammaglobin protein expressed by a tumor cell is detected in a sample using specific antibodies to the mammaglobin protein. The specific antibodies can be polyclonal or monoclonal antibodies.

The invention is also directed to novel compositions and methods for treating breast neoplastic disease using mammaglobin antigens capable of inducing an antibody-mediated and/or a cell-mediated, i.e., through activated T cells, immune response against a mammaglobin-expressing tumor.

One embodiment of a composition according to the invention comprises a mammaglobin B cell antigen capable of activating mammaglobin-specific B cells. The B cell antigen comprises a mammaglobin-specific B cell epitope and a $T_H$ epitope, or determinant, recognized by T helper cells.

In another embodiment, the mammaglobin antigen is a mammaglobin $T_C$ cell antigen recognized by mammaglobin-specific cytotoxic T lymphocytes which comprises a $T_C$ cell epitope and a binding site, or agretope, for a MHC class I molecule.

Yet another embodiment of a composition according to the invention comprises B cell and $T_C$ cell antigens.

Methods for treating a patient with a mammaglobin-expressing tumor include adoptive immunotherapy, which comprises ex vivo stimulation with a mammaglobin antigen of mammaglobin-specific lymphocytes isolated from the patient and subsequent administration of the activated lymphocytes to the patient, and in vivo stimulation of an anti-mammaglobin immune response, which comprises administering to the patient a vaccine comprising a mammaglobin antigen.

Among the several advantages found to be achieved by the present invention, therefore, may be noted the provision of a nucleotide sequence and encoded amino acid sequence that can serve as markers for breast cancer cells; the provision of methods for early detection of the presence of breast neoplasia cells; the provision of means for detecting breast cancer that can complement mammography and increase the predictive value; the provision of methods that can provide an estimation of prognosis; the provision of markers that will allow the targeting of therapy; and the provision of compositions for stimulating a cellular and humoral immune response against the tumor.

BRIEF DESCRIPTION OF THE DRAWINGS

FIG. 2 illustrates the human cDNA sequence (SEQ ID NO:1), (nucleotides numbered above) and the amino acid sequence of the encoded mammary-specific protein, mammaglobin (SEQ ID NO:2)(amino acids numbered below), the solid bar indicating the 403 bp fragment (SEQ ID NO:5) isolated by the RACE PCR method and the open bar indicating the 206 bp DEST002 sequence (SEQ ID NO:6);

FIG. 3 illustrates the amino acid sequence of the mammary-specific protein, mammaglobin (hMAM), (SEQ ID NO:2) compared to rat prostatic steroid binding protein subunit C3 (rPSC3)(SEQ ID NO:7) and human clara cell 10 kD protein (hCC10)(SEQ ID NO:8) with identities marked by bold letters and double lines and structurally similar amino acids marked by single lines;

FIG. 4 illustrates (FIG. 4A) the Northern blot analysis of hybridization of the human cDNA sequence encoding the mammary-specific protein, mammaglobin (hMAM), to mRNA expressed by tissues from breast neoplasia, normal breast and other adult tissues and (FIG. 4B) the analysis of RT/PCR amplified samples of tissues from breast neoplasia, normal breast and other adult tissues;

FIG. 13 shows a photograph of a northern blot of RNA from lymph node specimens containing histologically documented metastases from primary breast tumors (lanes 1–20, 27), squamous cell tumors of the head and neck (lanes 21, 23, 24), endometrial cancer (lane 22), adenocarcinoma of the colon (lane 25), billiary carcinoma (land 26), and adenocarcinoma of the lung (lane 28) and, as negative controls, lymph node biopsies from patients without any known malignancy (lanes 29–33) and as a positive control, a specimen from normal breast tissue (lane 34), and hybridized with the mammaglobin cDNA (top panels) or a keratin cDNA (bottom panels); and.

DESCRIPTION OF THE PREFERRED EMBODIMENTS

One aspect of the present invention is based upon the identification and sequencing of the cDNA identified as SEQ ID NO:1 which encodes a mammary-specific secretory protein, mammaglobin, identified by SEQ ID NO:2 (FIG. 2). As described below, the full length mamaglobin cDNA was isolated starting from tumor cell mRNA that was reverse transcribed, amplified using the technique of PCR and subcloned into expression vectors. In addition, the protein, mammaglobin, encoded by the cDNA was identified and characterized.

Figure 1:
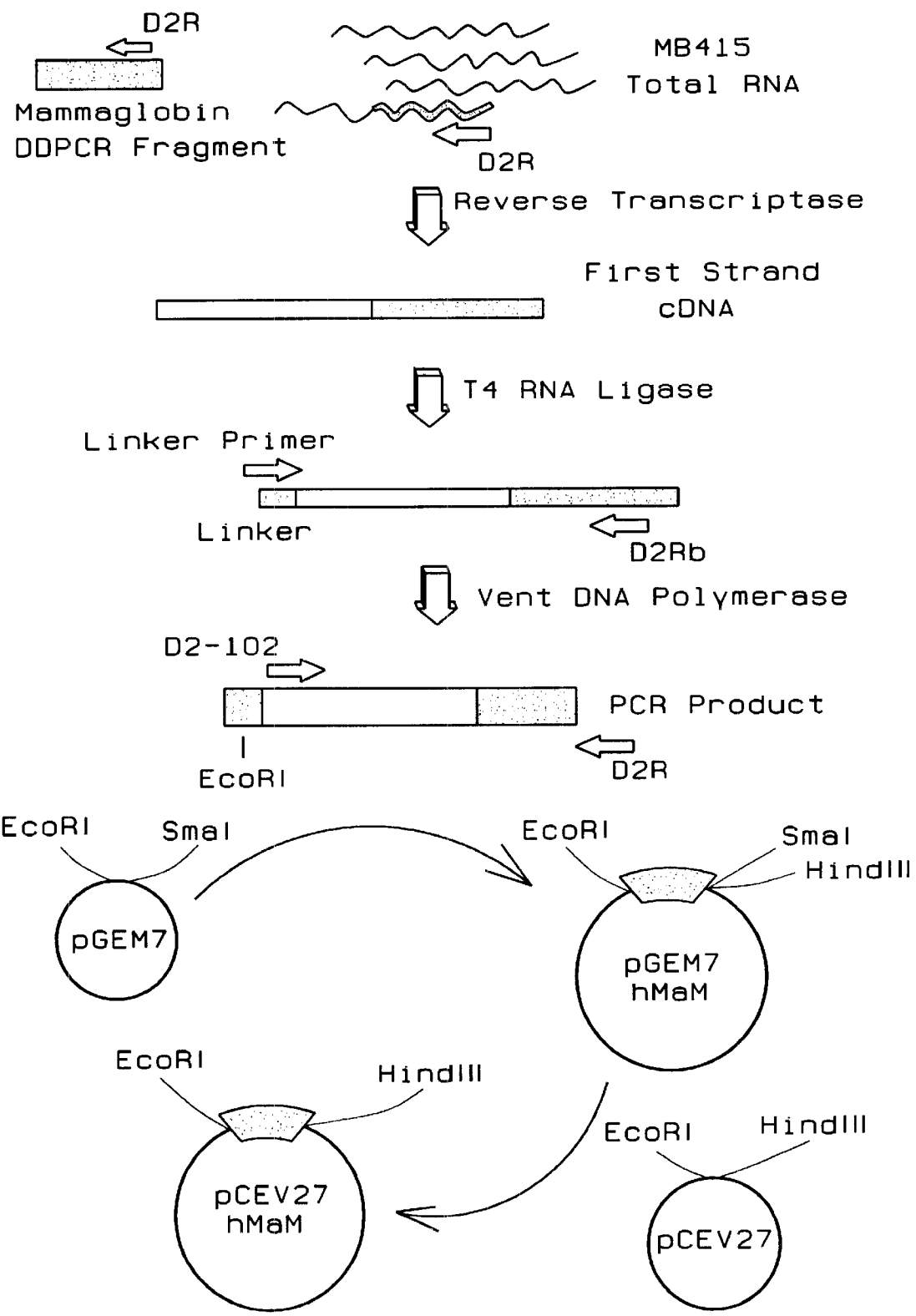
FIG. 1 illustrates the strategy used to isolate the full length mammaglobin cDNA including the Rapid amplification of cDNA Ends (RACE) Polymerase Chain Reaction (PCR) technique and subsequent subcloning into vectors pGEM7Z and pCEV27.

Using the anonymous sequence tag previously designated DEST002, it was demonstrated that the corresponding gene product, which was up until now unknown but herein identified as mammaglobin, is particularly abundant in the breast cancer tumor cell line MDA-MB-415. To isolate the full length mammaglobin cDNA, the mRNA was reverse transcribed from this cell line and cloned using the RACE PCR technique (Edwards et al. Nucleic Acids Research 19:5227–32, 1991). This technique is based upon the strategy of ligation of single-stranded oligodeoxyribonucleotide to the 3' end of single-stranded cDNA. The method by which the mammaglobin cDNA was isolated is represented schematically in FIG. 1.

The full length 503 bp cDNA sequence (SEQ ID NO:1) was deduced from the sequence information obtained from the 403 bp fragment (SEQ ID NO:5) (FIG. 2) isolated by this technique along with sequence information previously obtained from the corresponding DEST sequence (DEST002, SEQ ID NO:6) (FIG. 2) in our earlier study (Watson and Fleming, supra). Within the 503 bp cDNA is a 279 bp open reading frame (SEQ ID NO:15) which encodes a polypeptide of 93 amino acids (SEQ ID NO:2) (FIG. 2) and predicted molecular mass of 10.5 kD. The initial methionine of this open reading frame is within a near-perfect Kozak consensus sequence (Kozak, Cell 22:7–8, 1980). The 60 bp upstream of this sequence contain no other in-frame methionines or translational stops. The 3' untranslated sequence of the cDNA constitutes 163 bp and contains a polyadenylation signal, AATAAA, 12 bp upstream of the priming site of the original DEST002 sequence. These data indicate that the full length mammaglobin cDNA has been isolated. The first 19 residues of the encoded polypetide predict a hydrophobic peptide signal sequence and residues 53–55 and 68–70 are consensus N-linked glycosylation sites, indicating that mammaglobin is a secreted glycoprotein.

A search for DNA sequences similar to the mammaglobin cDNA sequence in Genbank using the BLAST algorithm (Benson et al., Nucl Acid Res 21:2963–2965, 1993; Altschul et al, J Mol Biol 215:403–410, 1990), identified no obvious DNA sequence homologies. Thus, mammaglobin cDNA is believed to be a novel, heretofore unknown DNA sequence.

A search of other polypeptides for sequences related to mammaglobin revealed an amino acid sequence homology between mammaglobin and other polypeptides. Mammaglobin exhibited 42% amino acid identity (58% including conservative substitutions) with rat prostatic steroid binding protein (prostatein) subunit C3 (rPSC3) (FIG. 3) (SEQ ID NO:7). Rat prostatic steroid binding protein is a major secretory protein in the rat ventral prostate consisting of a tetrameric protein composed of two different dimeric subunits; C3/C1 and C3/C2 (Parker et al., Ann N Y Acad Sci 438:115–124; Parker et al., J Steroid Biochem 20:67–71, 1984). The C1, C2, and C3 genes all encode approximately 6 kD secretory proteins and are thought to have arisen from gene duplication, but while the C1 and C2 genes show strong homology to each other, they are much less similar to the C3 gene. Correspondingly, mamaglobin shows no sequence homology with the C1 or C2 proteins.

As noted above, prostatic steroid binding protein (prostatein) is the major secretory protein in the rat ventral prostate and its expression is regulated by androgenic steroids (Parker et al, Ann N Y Acad Sci 438:115–24, 1984; Parker et al, J Steroid Biochem 20:67–71, 1984). Another protein, human estramustin-binding protein (hEMBP) has been reported to be expressed in human prostate, human breast cancer and human malignant melanoma. (Bjork et al, Cancer Res 42:1935–1942, 1982; Bjork et al, Anticancer Res 11:1173–82, 1991). Human estramustin-binding protein is immunochemically similar to rat estramustin-binding protein, which has been postulated to be identical to rat steroid-binding protein, prostatein. As noted above, the amino acid sequence of mammaglobin exhibited 42% amino acid identity and 58% homology including conservative substitutions with the C3 subunit of prostatein. Thus it is possible that mammaglobin could be in some way related to hEMBP. However, while both prostatein and hEMBP are detected in the prostate gland, mammaglobin mRNA is completely absent in this tissue. Hence, mammaglobin is neither the same protein nor a subunit of HEMBP and, furthermore, the sequence of hEMBP has not been determined so that it is not known whether there is even any similarity of mammaglobin with some fragment or subunit of HEMBP.

Although recent reports have demonstrated the rPSC3 promoter fused to SV40 T antigen produces both prostatic and mammary carcinomas in transgenic mice (Maroulakou et al., Proc Nat Acad Sci U.S. 91:11236–11240, 1994; Sandmoller et al, Oncogene 9:2805–2815, 1994), the true biological function of this protein is unknown. Furthermore, notwithstanding the hypothesized relationship of rat prostatic steroid binding protein to human EMBP, no human polypeptide or human gene corresponding to rPSC3 has been identified. Thus, mammaglobin and the cDNA encoding mammaglobin represent novel sequences heretofore unknown.

Using manual alignment with other sequences that had less significant BLAST scores with both mammaglobin and rPSC3 protein sequences, we identified other homologies with human clara cell 10 kD protein (hCC10) (SEQ ID NO:8) (Peri et al, *J Clin Invest* 92:2099–2109, 1993) (FIG. 3) and, in addition, with rabbit and mouse uteroglobin proteins (Miele et al., *Endocrine Rev* 8:474–90, 1987; Cato and Beato, *Anticancer Res* 5:65–72, 1985; Miele et al., *J Endocrinol Invest* 17:679–692, 1994). These homologies, depending on species, were 26% identity or 40% including conservative substitutions. In particular, a number of amino acids were perfectly conserved among all proteins, including Cys-3 and Cys-69 which are known to play a role in disulfide bond formation between uteroglobin subunits (see below). These homologies suggest that mammaglobin is a novel member of a small family of proteins that are secreted by epithelial cells (Miele et al, 1994, supra).

The hCC10 gene is the human homologue of rabbit and mouse uteroglobin genes (Peri et al, *J Clin Invest* 92:2099–2109, 1993). Uteroglobin was originally characterized as a secretory protein in rabbit uterus, but has since been found in other epithelial organs including lung, breast and prostate. Unlike rat prostatein, uteroglobin is a homodimeric protein coupled by two disulfide linkages at the conserved residues Cys-2 and Cys-69 (Miele et al, 1994, supra). Although uteroglobin gene transcription is regulated by steroid hormones, the ability of the protein itself to bind progesterone or other steroid hormones is controversial and again, the true biological function of this protein is unknown (Miele et al., 1994, supra).

Mammaglobin expression is restricted to the mammary gland. This is in contrast to the observation that rPSC3 is expressed in rat ventral prostate (Parker et al., *Ann N Y Acad Sci* 438:115–1124, 1984), and the expression of hCC10/uteroglobin in numerous tissues including lung, uterus, prostate, and breast (Miele et al., 1987, supra; Cato and Beato, supra; Miele et al., 1994 supra). Because of the sequence homology between mammaglobin and these proteins, we determined the pattern of tissue specific expression.

The 500 bp mammaglobin mRNA was easily detected in tumor specimen 2410 (the tissue from which this original sequence tag was isolated) and to a much less extent in normal human breast tissue (FIG. 4A). Mammaglobin mRNA could not be detected in the immortalized breast epithelial cell line B5-589. Expression of mammaglobin was also undetectable in human uterus and lung, two sites of uteroglobin expression.

Amplification using RT/PCR detected mammaglobin mRNA in both tumor 2410 and normal breast tissue, but not in 15 other tissues surveyed, including tissues that normally express rPSC3 and uteroglobin (lung, uterus, prostate), hormonally responsive and steroidogenic tissues (ovary, testis, placenta), and other secretory epithelial organs (colon) (FIG. 4B). Therefore, the expression of mammaglobin mRNA is relatively specific for mammary tissue.

To unequivocally demonstrate the breast-specific nature of mammaglobin expression, the full-length mammaglobin cDNA was used to probe for mammaglobin mRNA in a more extensive and quantitative panel of polyA-selected mRNAs from pooled populations of adult and fetal human tissues as described below in Example 2A. Mammaglobin mRNA expression was completely absent in other closely related apocrine glands such as the salivary gland and was also undetectable in peripheral leukocytes, lymph node, and bone marrow. Apart from the mammary gland, mammaglobin mRNA was not detected in any other of the 43 adult or seven fetal tissues surveyed. This confirms that mammaglobin gene expression is likely to be a very specific marker for breast cancer.

Based on the studies in this report, mammaglobin is a relatively mammary-specific protein. Two other genes known to be overexpressed in breast carcinoma are erb-B and cyclin D (Jardines et al, *Pathobiology* 61:268–282, 1994; Keyomars and Pardee, *Proc Nat Acad Sci U.S.* 90:1112–1116, 1993). Unlike the overexpression of erb-B or cyclin D, the overexpression of mammaglobin may reflect a more specific alteration of the mammary epithelial cell rather than a general increased growth potential or mitotic rate. As such, appearance of mammaglobin gene dysregulation may have more specific import for the therapeutic vulnerability or clinical course of a tumor.

As reported in U.S. Pat. No. 5,668,267, overexpression of mammaglobin mRNA was detected by northern blot hybridization in the 2410 tumor specimen as well as 4 of 15 (27%) stage 1 primary breast carcinomas of differing histological types. This percentage is comparable to the prevalence of other genetic alterations such as erb-B amplification and p53 mutation (Slamon et al. *Sci* 244:707–712, 1989; Thor et al, *J Nat'l Cancer Inst* 84:845–855, 1992). Furthermore, because we have restricted our analysis to stage I tumors, overexpression of mammaglobin would actually be more prevalent than any other genetic alteration reported in this subgroup of tumors (Alllerd et al, *J Nat'l Cancer Inst* 85:200–206, 1993). These data suggest that overexpression of mammaglobin is not unique to a single tumor specimen and is, in fact, relatively frequent among primary breast tumors. Furthermore, the fact that all tumors examined were stage I suggests that this dysregulation occurs relatively early in the progression of breast neoplasia.

Mammaglobin expression could not be detected in normal lymph nodes or peripheral lymphocytes at the level of sensitivity afforded by a single step RT/PCR assay. However, as reported below, mammaglobin mRNA was detected in over 40% of lymph nodes and in 60% of peripheral blood stem cell collections (PBSCs) from patients with metastatic breast cancer. These results indicate that analysis of mammaglobin transcripts in peripheral lymph nodes and blood stem cells may be useful for detecting occult breast cancer metastases, as has been suggested for other epithelial specific genes (Schoenfeld et al., *Cancer Res* 54:2986–2990, 1994).

Figure 5:
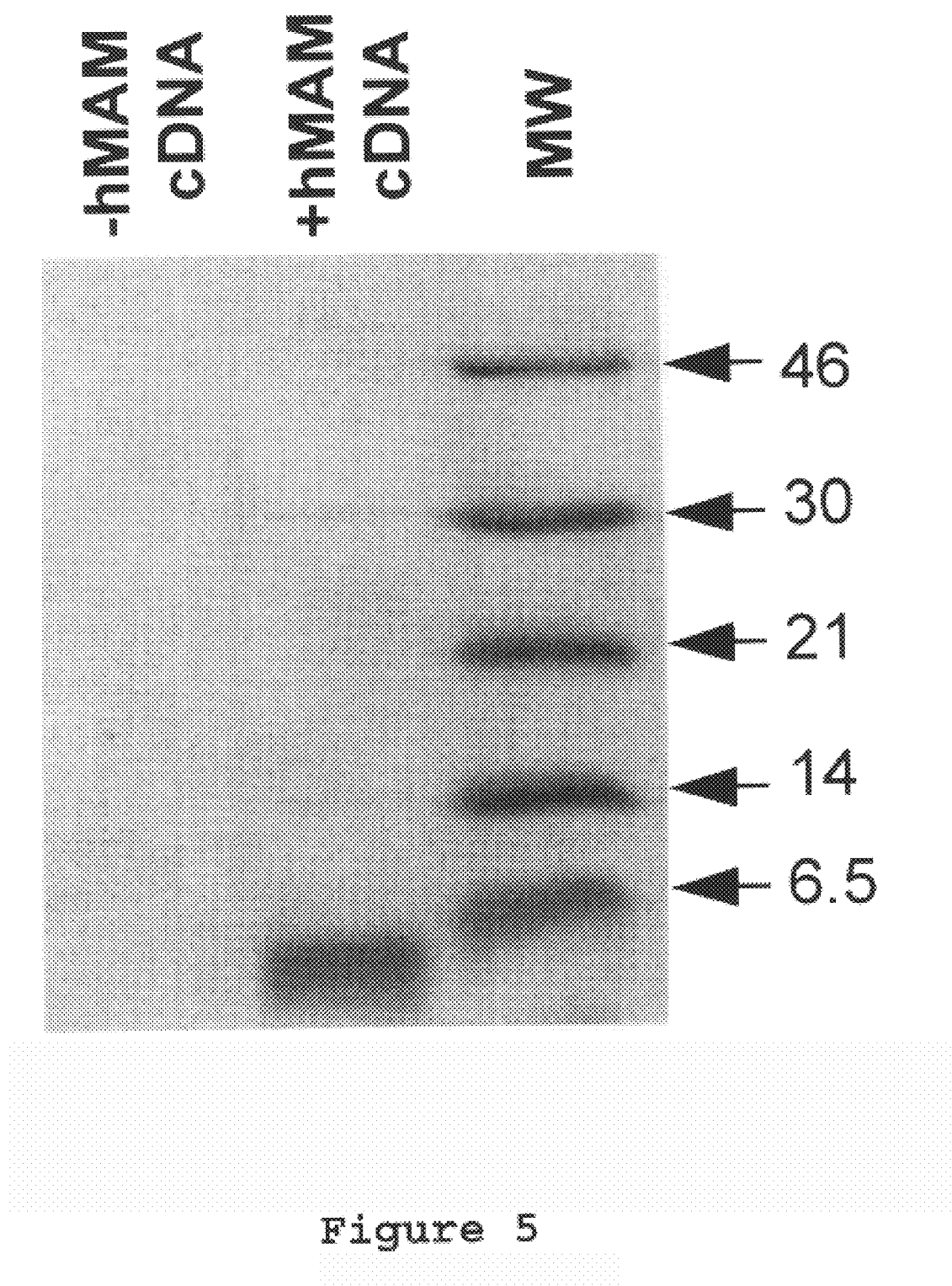
FIG. 5 illustrates the translation of the mammary-specific cDNA sequence in an in vitro rabbit reticulocyte lysate assay system.

To demonstrate that the mammaglobin cDNA encoded a translatable protein, the cDNA clone was used in an in vitro translation assay. FIG. 5 shows the protein product from a rabbit reticulocyte lysate programmed with the mammaglobin cDNA. An approximately 6 kD protein is generated using the mammaglobin cDNA. The apparent molecular weight is smaller than that predicted from conceptual translation of the open reading frame, but this finding is commonly observed with rabbit and human uteroglobin translation products as well.

To examine the prevalence of mammaglobin protein expression in breast cancer, rabbit polyclonal, anti-mammaglobin antibody was generated against a peptide corresponding to the C-terminal mammaglobin protein sequence and used to examine 100 primary breast tumors of multiple grades and histological types for mammaglobin protein expression by immunohistochemical analysis. As summarized in Table 1 below, over 80% of these tumors were strongly immunopositive for mammaglobin protein and staining was independent of tumor grade. This result indicates that detection of mammaglobin protein in clinical samples can be used as a sensitive and specific marker for primary breast cancer.

Because Applicants believe mammaglobin is a secreted protein, its presence would be expected to be detectable in sera from patients whose tumors overexpress this gene product. As such, mammaglobin is likely to be as clinically useful as prostate specific antigen (PSA) and other solid tumor markers for managing patients with breast cancer (Tumor markers in diagnostic pathology, *Clin Lab Med* 10:1–250, 1990).

The identification of mammaglobin as a breast cancer marker provides the basis for another aspect of the present invention, which involves methods for detecting the presence of breast cancer in a patient. The term "detection" as used herein in the context of detection of breast neoplastic disease is intended to be a comprising aspect of the determining of the presence of breast cancer in a patient, the distinguishing of breast cancer from other diseases, the estimation of prognosis in terms of probable outcome of the disease and prospect for recovery, the monitoring of the disease status or the recurrence of the disease, the determining of a preferred therapeutic regimen for the patient and the targeting of antitumor therapy.

One method for detecting breast cancer comprises hybridizing a polynucleotide to mRNA from breast neoplasia cells. The polynucleotide comprises the complement of SEQ ID NO:15 or a derivative of the complement of SEQ ID NO:15. As used herein, a polynucleotide includes DNA and/or RNA and thus the nucleotide sequences recited in the Sequence Listing as DNA sequences also include the identical RNA sequences with uracil substituted for thymine residues. A derivative of a nucleotide sequence has sufficient sequence identity to the sequence from which it is derived to specifically hybridize to mammaglobin mRNA from breast neoplasia cells under the same stringency conditions that the sequence from which it is derived specifically hybridizes to the mammaglobin mRNA from breast neoplasia cells. The derived nucleotide sequence is not necessarily physically derived from the nucleotide sequence, but may be generated in any manner including for example, chemical synthesis or DNA replication or reverse transcription or transcription. Preferred derivative nucleotide sequences include fragments of the complement of SEQ ID NO:15 and sequences identical to the complement of an allelic variant of the mammaglobin coding sequence set forth in SEQ ID NO:15.

To detect the presence of mRNA encoding mammaglobin in a detection system for breast cancer, a sample is obtained from a patient. The sample can be a tissue biopsy sample or a sample of blood, plasma, serum or the like. The sample may be treated to extract the nucleic acids contained therein. Preferably, the resulting nucleic acid from the sample is subjected to gel electrophoresis or other size separation techniques.

Detection involves contacting the nucleic acids and in particular the mRNA of the sample with the polynucleotide probe to form hybridization duplexes. The term "probe" refers to a structure comprised of a polynucleotide which forms a hybrid structure with a target sequence, due to complementarily of probe sequence with a sequence in the target region.

Detection of the resulting duplex can be accomplished by any known methodology. The hybridization duplex is usually accomplished by the use of labeled probes. Alternatively, the probe may be unlabeled, but may be detectable by specific binding with a ligand which is labeled, either directly or indirectly. Suitable labels and methods for labeling probes and ligands are known in the art, and include, for example, radioactive labels which may be incorporated by known methods (e.g., nick translation or kinasing), biotin, fluorescent groups, chemiluminescent groups (e.g., dioxetanes, particularly triggered dioxetanes), enzymes, antibodies, and the like.

When probing with a mammaloglobin cDNA, high stringency conditions can be used in order to prevent false positives. When using a probe containing a sequence derived from the complement of the mammaglobin coding sequence, less stringent conditions can be used. The stringency of hybridization is determined by a number of factors during hybridization and during the washing procedure, including temperature, ionic strength, length of time and concentration of formamide. These factors are outlined in, for example, Sambrook et al. (*Molecular Cloning: A Laboratory Manual,* 2d ed., 1989).

In order to increase the sensitivity of detection of mammaglobin mRNA in a sample, the technique of reverse transcription/polymerization chain reaction (RT/PCR) can be used to amplify cDNA transcribed from mRNA encoding mammaglobin. The method of RT/PCR is well known in the art (for example, see Watson and Fleming, supra). Oligonucleotides useful as the amplification primers comprise SEQ ID NO:3 and SEQ ID NO:4. Preferably, the mammaglobin forward amplification primer consists of 5'-AGCACTGCTACGCAGGCTCT-3' (SEQ ID NO:16) and the mammaglobin reverse amplification primer consists of 5'-ATAAGAAAGAGAAGGTGTGG-3' (SEQ ID NO:4).

Alternatively, a mammaglobin target sequence in the reverse transcribed cDNA can be amplified and detected using any other known methodology such as ligase chain reaction methods, including gap LCR (G-LCR) and other variations, or self-sustained sequence replication (3SR) and its various modifications. In addition, the mammaglobin mRNA can be detected directly by asymmetric gap LCR (AG-LCR). See, e.g., Leckie et al., "Infectious Disease Testing by Ligase Chain Reaction" in *Molecular Biology and Biotechnology*, R. A. Myers, ed., pp. 463–466, VCH Publishers, 1995.

In another embodiment of the present invention, the mammaglobin cDNA sequence or derivative thereof can be used to characterize any alteration of the mammaglobin gene (i.e. gene rearrangement, gene amplification, or gene deletion) in a specimen from a breast-cancer patient. This provides a method whereby patient specimens or samples, which do not contain intact mRNA, can still be examined for changes in gene structure.

In one application of this technique, the mammaglobin cDNA sequence or derivative thereof is hybridized to patient genomic DNA that has been isolated from a patient's tumor, normal tissue, or lymphocytes and digested with one or more restriction endonucleases. Using the Southern blot protocol, which is well known in the art, this assay determines whether a patient or a patient's breast tumor has a mammaglobin gene, which was deleted, rearranged, or amplified. Detection of these changes can then provide important information useful for predicting prognosis and for patient management.

In a second application of this technique, one or more pairs of oligonucleotide primers based on the mammaglobin cDNA sequence and complement thereof could be used in the polymerase chain reaction to amplify segments of the mammaglobin gene from a patient sample. Analysis of the resulting PCR products indicate whether a particular segment of the mammaglobin gene is deleted or rearranged. Such information is useful for prognosis and patient management.

Another method for detecting breast cancer comprises detecting the presence of the precursor and/or secreted forms of the mammaglobin polypeptide in a sample obtained from a patient. Any method known in the art for detecting proteins can be used. Such methods include, but are not limited to immunodiffusion, immunoelectrophoresis, immunochemical methods, binder-ligand assays, immunohistochemical techniques, agglutination and complement assays. (for example see *Basic and Clinical Immunology*, Sites and Terr, eds., Appleton & Lange, Norwalk, Conn. pp 217–262, 1991). Preferred are binder-ligand immunoassay methods including reacting antibodies with an epitope or epitopes of mammaglobin and competitively displacing a labeled mammaglobin polypeptide or derivative thereof.

As used herein, the term "mammaglobin polypeptide" embraces naturally occurring mammaglobin, including non-glycosylated and glycosylated precursor forms and the glycosylated secreted form, derivatives and fragments thereof. By naturally occurring is meant a polypeptide that can be isolated from a source in nature, e.g., from normal and/or diseased organisms, and that has not been intentionally modified by man. Naturally-occurring mammaglobin polypeptides identified herein include a precursor form which comprises SEQ ID NO:2 and a secreted form comprising SEQ ID NO:17 (amino acids 20–93 of SEQ ID NO:2). Allelic variants of SEQ ID NO:2 are also intended to be included in the scope of naturally-occurring mammaglobin polypeptides.

A derivative of a mammaglobin polypeptide is intended to refer to polypeptides which are comprised of a segment of at least 10 amino acids that has substantial identity to a portion of naturally occurring mammaglobin. The segment having substantial identity is preferably at least about 20 amino acids, more preferably at least about 50 amino acids, and most preferably at least about 75 amino acids. Two polypeptides have substantial identity when upon optimal alignment by sequence alignment programs such as BLAST using default settings for gap penalties and other parameters, they share at least 80% sequence identity, preferably at least 90% sequence identity, more preferably at least 95% sequence identity, most preferably 99% sequence identity. Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acid substitution groups are: valine-leucine-isoleucine, phenylalanine-tyrosine, lysine-arginine, alanine-valine, and asparagine-glutamine.

A derivative mammaglobin polypeptide will preferably cross-react with an anti-mammaglobin antibody, monoclonal or polyclonal, which is specific for naturally occurring mammaglobin or fragments thereof.

As used herein the terms "fragment" and "peptide" refer to a mammaglobin polypeptide having an amino acid sequence identical to the amino acid sequence deduced from a full-length mammaglobin cDNA (e.g., SEQ ID NO:1), but that has an amino-terminal and/or carboxy-terminal deletion. Typically, mammaglobin fragments or peptides are at least 3 amino acids long. Preferably a mammaglobin fragment or peptide is at least 6 amino acid residues in length, more preferably about 12 amino acid residues in length, even more preferably about 25 amino acid residues in length, and most preferably 50 amino acid residues or greater.

Numerous competitive and non-competitive protein binding immunoassays are well known in the art. Antibodies employed in such assays may be unlabeled, for example as used in agglutination tests, or labeled for use in a wide variety of assay methods. Labels that can be used include radionuclides, enzymes, fluorescers, chemiluminescers, enzyme substrates or co-factors, enzyme inhibitors, particles, dyes and the like for use in radioimmunoassay (RIA), enzyme immunoassays, e.g., enzyme-linked immunosorbent assay (ELISA), fluorescent immunoassays and the like.

Polyclonal or monoclonal antibodies to a mammaglobin polypeptide comprising a B cell epitope can be made for use in immunoassays by any of a number of methods known in the art. As used herein, the term "B cell epitope" refers to an antigenic determinant of a mammaglobin polypeptide. The B cell epitope could comprise 3 amino acids in a spatial conformation which is unique to the epitope. Generally, a B cell epitope consists of at least 5 such amino acids. Methods of determining the spatial conformation of amino acids are known in the art, and include, for example, x-ray crystallography and 2 dimensional nuclear magnetic resonance.

One approach for preparing antibodies to a protein is the selection and preparation of an amino acid sequence of all or part of the protein, chemically synthesizing the sequence and injecting it into an appropriate animal, usually a rabbit or a mouse.

Methods for preparation of a mammaglobin polypeptide include, but are not limited to chemical synthesis, recombinant DNA techniques or isolation from biological samples. Chemical synthesis of a peptide comprising an epitope can be performed, for example, by the classical Merrifeld method of solid phase peptide synthesis (Merrifeld, *J Am Chem Soc* 85:2149, 1963) or the FMOC strategy on a Rapid Automated Multiple Peptide Synthesis system (DuPont Company, Wilmington, Del.) (Caprino and Han, *J Org Chem* 37:3404, 1972).

Polyclonal antibodies can be prepared by immunizing rabbits by injecting antigen into the popliteal lymph nodes followed by subsequent boosts at two week intervals with intraperitoneal injection of antigen. The animals are bled and sera assayed against purified mammaglobin protein, usually by ELISA. Monoclonal antibodies can be prepared after the method of Milstein and Kohler by fusing splenocytes from immunized mice with continuously replicating tumor cells such as myeloma or lymphoma cells. (Milstein and Kohler *Nature* 256:495–497, 1975; Gulfre and Milstein, *Methods in Enzymology: Immunochemical Techniques* 73:1–46, Langone and Banatis eds., Academic Press, 1981). The hybridoma cells so formed are then cloned by limiting dilution methods and supernates assayed for antibody production by ELISA or RIA.

Thus prepared polyclonal or monoclonal antibodies to mammaglobin may be used to isolate and purify precursor and secreted forms of mammaglobin from cells expressing mammaglobin. For example, as shown below, a polyclonal antibody generated against the 16 C-terminal amino acids predicted from mammaglobin cDNA (Glu-Val-Phe-Met-Gln-Leu-Ile-Tyr-Asp-Ser-Ser-Leu-Cys-Asp-Leu-Phe, SEQ ID NO:14) binds to precursor and secreted forms of mammaglobin, as well as to mammaglobin that has been synthesized in an in vitro translation system. Isolation of mammaglobin using an anti-mammaglobin antibody may be accomplished using procedures well-known in the art, such as affinity chromatography.

The unique ability of antibodies to recognize and specifically bind to target antigens expressed by a tumor cell provides an approach for the treatment of cancer. (For review see LoBuglio and Saleh, *Am J Med Sci* 304:214–224, 1992; Bagshawe, *Adv Pharmacol* 24:99–121, 1993). Thus, another aspect of the present invention provides for a method for preventing the onset and treating breast cancer in an animal based upon the use of antibodies to mammaglobin, which has been discovered to be overexpressed by breast cancer cells.

Specific antibodies to mammaglobin, either polyclonal or monoclonal, are produced by any method known in the art. For example, murine or human monoclonal antibodies can be produced by hybridoma technology. Alternatively, mammaglobin, or an immunologically active derivative or fragment thereof, or an anti-idiotypic antibody, or fragment thereof, can be administered to an animal to elicit B cell production of antibodies capable of recognizing the mammaglobin-expressing cells.

The antibodies so produced or fragments thereof are labeled with one or more oncolytic substances such as radionuclides, toxins, or cytotoxic drugs and administered to a patient suspected of having breast cancer. The binding of the labeled antibody to the mammaglobin being overexpressed by the breast cancer cell will cause the death of the cancer cell.

Any of a variety of oncolytic substances known in the art can be used to produce such labeled antibodies. For example, immunotoxins can be made by coupling plant and bacterial toxins to antibodies. Such toxins include, for example, ricin, diphtheria toxin and Pseudomonas exotoxin A. Drug-antibody conjugates can also be made in which chemotherapeutic agents are linked to the antibody. Chemotherapeutic agents suitable for such use include, for example, tomoxifen, doxorubicin, methotrexate, chlorambucil, Vinca alkaloids, and mitomycin. In addition, radioimmunoconjugates can be made in which a radionuclide is stably linked to the antibody. Radionuclides suitable for making radioimmunoconjugates include, for example, β-emmitters such as $^{131}$I, $^{188}$Re, $^{186}$Re, $^{67}$Cu, $^{90}$Y and $^{47}$Sc; α-emitters such as $^{211}$At, $^{212}$Bi and $^{212}$Pb; auger electron emitters such as 125I and $^{77}$Br; and fissionable nuclides such as $^{10}$B.

The finding that a significant percentage of breast tumors express mammaglobin protein is the basis for another aspect of the invention, which involves the activation of mammaglobin-specific B and/or T cell lymphocytes ($T_C$) with mammaglobin antigens. Accordingly, the invention provides mammaglobin B cell antigens and $T_C$ cell antigens; vaccines comprising at least one B cell mammaglobin antigen and/or at least one $T_C$ mammaglobin antigen for inducing antibody- and/or cell-mediated immune responses against mammaglobin-expressing tumors, and methods for treating a breast cancer patient with a mammaglobin-expressing tumor. One method according to the invention comprises administering to the patient activated mammaglobin-specific lymphocytes. Another method comprises administering to the patient a mammaglobin-specific vaccine.

As used herein, "mammaglobin antigen" includes naturally occurring mammaglobin polypeptides, derivatives, and fragments thereof which contain a B cell or $T_C$ cell epitope recognized by mammaglobin-specific B cells or $T_C$ cells.

A mammaglobin B cell antigen comprises a mammaglobin-specific B cell epitope and a $T_H$ cell epitope. The term "B-cell epitope" refers to any antigen, hapten, epitope or antigenic determinant which is recognized by anti-mammaglobin immunoglobulin receptors on B cells and is capable of eliciting the production of antibodies with appropriate help from $T_H$ cells when administered to an animal. The B cell epitope comprises an amino acid sequence of at least 4 amino acids. Preferably, the B cell epitope is between at least 6 and 25 amino acids in length and more preferably is between about 15 and 22 amino acids in length. The comprising amino acid sequence of the B cell epitope may be identical or substantially identical to a continuous amino acid sequence in a fragment of naturally occurring mammaglobin. Alternatively, the comprising amino acid sequence of a B cell epitope is identical to or substantially identical to a discontinuous amino acid sequence representing an assembled topographic determinant of mammaglobin.

The term "$T_H$ cell epitope" refers to any antigenic determinant recognized by T helper cells through association with MHC class II molecules. The activation of T helper cells induces differentiation of resting mammaglobin-specific B cells into higher affinity IgG-secreting cells, i.e, induces a secondary antibody response. The preparation and use of immunogenic peptides containing B and $T_H$ cell determinants to produce higher titres of specific antibody-producing B cells through T cell help is known in the art, see, e.g., Cheronis et la., U.S. Pat. No. 5,573,916, Denton, et la., *Cancer Letters* 70:143–150 (1993), Borras-Cuesta et al., *Eur. J Immunol.* 17, 1213–1215 (1987), and Good et al., *Science* 235:1059–1062 (1987). The $T_H$ cell epitope may comprise an amino acid sequence from mammaglobin or a heterologous protein. For example, Denton et al. describe the induction of antibody responses to mucins, which are complex glycoproteins expressed in secretory epithelia and associated with breast and other carcinomas, in mice immunized with a synthetic peptide containing a B cell determinant region from the core of MUC-1 mucin linked to sequence 111–120 of influenza haemagglutinin A/X-3 1, a known helper T cell-determinant. The $T_H$ cell epitope comprises an amino acid sequence of between about 6 to about 20 amino acid residues, preferably between about 8 residues and 18 residues, even more preferably between 9 residues and 15 residues.

A mammaglobin $T_C$ cell antigen comprises a $T_C$ cell epitope and a MHC class I agretope. The term "$T_C$ cell epitope" means any antigen, epitope or antigenic determinant which is recognized by mammaglobin-specific $T_C$ cells when presented by a MHC class I molecule on the surface of an antigen presenting cell. The term "MHC class I agretope" refers to any amino acid sequence recognized by a MHC class I molecule that allows the mammaglobin antigen to be presented to a mammaglobin-specific $T_C$ cell by the MHC class I molecule on an antigen presenting cell (APC). The $T_C$ cell epitope and MHC class I agretope are contained within an amino acid sequence of between about 6 to about 11 amino acids that is identical or substantially identical to the amino acid sequence of a fragment of naturally occurring mammaglobin. Preferably, the sequence is 8 or 9 amino acids in length.

Methods for identifying B and $T_C$ cell epitopes for a protein antigen are known in the art. For example, the capacity of isolated mammaglobin-specific B cells or mammaglobin-specific $T_C$ cells to respond to overlapping synthetic peptides spanning secreted mammaglobin may be determined using standard immunobiology techniques. Those peptides identified as antigenic may then be modified one or a few amino acids at a time to optimize their ability to stimulate mammaglobin-specific B or T cells.

B cell epitopes can also be mapped using commercially available epitope mapping kits which involve the screening of random peptides bound at the C terminus to polyethylene multipin supports, e.g., Cambridge Research Biochemicals.

Alternatively, the predicted mammaglobin amino acid sequence may be searched for sequences that conform to known binding motifs of MHC class I or MHC class II molecules. See e.g, Hill et al., *Nature* 360:434 (1992), Pamer et al., *Nature* 360:852 (1992) and Hammer et al., *J. Exp. Med.* 176:1007 (1992), and Falk et al., *Nature* 351:290–296 (1991). For example, antigenic peptides recognizable by breast tumor-specific CTLs may be identified by searching the mammaglobin amino acid sequence for HLA-A2-binding peptides as described by Peoples et al., *Proc. Natl. Acad. Sci.* 92:432–436 (1995). The choice of HLA-A2 as the antigen presenting molecule is appropriate where the patient expresses HLA-A2 (approximately 50% of Caucasians express HLA-A2). The predicted HLA-A2 binding peptides can be synthesized and tested for antigenicity by loading the synthetic peptides onto the T2 cell line, a human T-cell/B-cell fusion product containing a defect in antigen presentation such that HLA-A2 molecules on the surface of T2 cells can be effectively loaded with exogenous HLA-A2 binding peptides (Henderson, et al, Science 255:1264–1266 (1992)). A standard cytotoxicity assay is then carried out which comprises incubating the peptide-loaded T2 cells with breast-specific CTLs derived from tumor infiltrating lymphocytes (TILs) isolated from a mammaglobin-expressing breast tumor, e.g., see Peoples et al., pages 432–433 and Toso et al., *Cancer Research* 56:16–20 (1996).

Antigenic mammaglobin peptides containing $T_C$ cell epitopes may also be identified by acid-eluting endogenous peptides presented by HLA class I molecules on the tumor cell surface. (See, e.g., Peoples et al., supra, p. 433). The eluted peptides may be separated by any number of techniques known in the art, including HPLC fractionation. The different peptide fractions are loaded onto T2 cells and the loaded T2 cells are incubated with breast-tumor specific CTLs to determine which peptides are recognized by the CTLs using standard immunobiology techniques.

One use of a mammaglobin antigen according to the invention is in adoptive immunotherapy. This therapy involves in vitro activation and expansion by a mammaglobin antigen of anti-mammaglobin antibody-producing B cells and/or mammaglobin-specific cytotoxic T lymphocytes (CTLs) isolated from a patient with a mammaglobin-expressing tumor. The method may also be practiced with a composition comprising both mammaglobin B cell and $T_C$ cell antigens. The activated lymphocytes are then introduced back into the patient for adoptive immunotherapy.

A mammaglobin antigen according to the invention is also useful as a component of a mammaglobin-specific vaccine. The vaccine comprises an immunogenically-stimulatory amount of a mammaglobin antigen. As used herein, an immunostimulatory amount refers to that amount of antigen that is able to stimulate the desired immune response in the recipient for the amelioration, or treatment, of breast cancer. This amount may be determined empirically by standard procedures, well known to those of ordinary skill in the art, without undue experimentation.

The antigen may be provided in any one of a number of vaccine formulations which are designed to induce the desired type of immune response, e.g., antibody and/or cell mediated. Such formulations are known in the art. See, e.g., A. Lanzavecchia, *Science* 260:937–944 (1993) and U.S. Pat. No. 5,585,103 to Raychandhuri. Examples of vaccine formulations used to stimulate immune responses include pharmaceutically acceptable adjuvants such as aluminum salts; emulsions of squalene or squalane and muramyl dipeptide; liposomes; and a composition comprising a stabilizing detergent, a micelle-forming agent, and a biodegradable and biocompatible oil (Raychandhuri, supra).

A mammaglobin-specific vaccine may also comprise a carrier cell loaded with a mammaglobin antigen. Preferably, the carrier cell is prepared from autologous professional antigen presenting cells (APC) such as macrophages, dendritic cells, or activated B or T lymphocytes. See e.g., Lanzavecchia, supra, p. 937. Professional APCs express a ligand, B7, that binds to CD28 or CTLA4 on T cells to deliver an antigen- nonspecific costimulatory signal known as Signal 2 which prevents T cell anergy or inactivation. Thus, the vaccine may also comprise interleukin-2 or another costimulatory signal to counteract anergy induction. (Lanzavecchia, supra, p. 938.)

Another formulation of a mammaglobin-specific vaccine comprises a recombinant vector containing a nucleotide sequence encoding for expression a mammaglobin antigen. The use of infectious agents to stimulate cytotoxic T lymphocytes is known in the art. (Raychaudhuri, supra.) Chimeric vectors have been described using vaccinia, polio, adeno- and retro-viruses, as well as bacteria such as Listeria and BCG. For example, a canarypox virus vector, ALVAC, has been shown to elicit strong cellular immune responses against encoded heterologous gene products (Taylor et al, *Virology* 187:321–328 (1991)). In addition, a recombinant ALVAC expressing the MZ2-E human melanoma rejection antigen encoded by the MAGE-1 gene is able to stimulate in vitro MAGE-1 CTL activities in a TIL population derived from a breast tumor expressing MAGE-1 mRNA(Toso et al, supra). In another approach described in U.S. Pat. No. 5593972 to Weiner et al, a recombinant expression vector encoding an antigen of an immunogenic protein to be targeted is directly administered to an individual either in vivo, e.g., to muscle cells, or to the cells of an individual ex vivo along with an agent that facilitates uptake of the DNA into the cells.

Those skilled in the art may readily determine how to formulate a vaccine suitable for achieving the desired immune response. For example, for inducing in vivo production of anti-mammaglobin antibodies, a mammaglobin-specific vaccine comprises at least one mammaglobin B cell antigen comprising a B cell epitope and a $T_H$ cell epitope. The $T_H$ cell epitope is preferably matched with the appropriate MHC class II haplotype of the intended vaccine recipient. Alternatively, a $T_H$ cell epitope could be used that is known to be recognized universally by humans regardless of HLA type such as the "universal" T cell epitope from tetanus toxoid (Panina-Bordignon et al. *Eur. J. Immunol.* 19:2237 (1989). Preferably, the vaccine comprises a plurality of mammaglobin B cell antigens with $T_H$ epitopes recognized by MHC Class II molecules of different HLA types.

Another embodiment of a mammaglobin-specific vaccine induces a cell-mediated response and comprises at least one mammaglobin $T_C$ antigen capable of activating mammaglobin-specific $T_C$ cells. Preferably, the vaccine comprises several $T_C$ cell antigens.

A mammaglobin-specific vaccine may also be formulated to induce both antibody and cell-mediated responses. This embodiment comprises both mammaglobin B cell and $T_C$ cell antigens.

A patient with a mammaglobin-expressing tumor may be treated by administering to the patient an immunostimulatory amount of a mammaglobin-specific vaccine according to the present invention. Administration of the vaccine may be by any known or standard technique. These include, but are not limited to intravenous, intraperitoneal, intramuscular, subcutaneous, or intramammary injection.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

In the examples below, cell lines were obtained from American Type Culture Collection and grown in Dulbecco's minimal essential medium supplemented with 10% fetal calf serum. Tissue biopsy specimens were obtained from the Human Cooperative Tissue Network (LiVolsi et al, *Cancer* 71:1391–1394, 1993).

EXAMPLE 1

This example illustrates the isolation of mammaglobin cDNA.

Total cellular RNA from the cell line MDA-MB415 was isolated using the standard guanidinium isothiocyanate method. (Belyavsky et al, supra). This RNA was used in the RACE PCR procedure employing the Amplifinder kit (Clonetech) and following the manufacturer's protocol.

The synthesis of first strand cDNA was performed in a standard reaction containing 1 µg RNA, 10 µM specific mammaglobin primer D2R (5'-ATA AGA AAG AGA AGG TGT GG-3')(SEQ ID NO:4), 4 µl of 5×RT buffer (250 mM TrisCl pH8.3, 375 mM Kcl, 15 mM MgCl₂), 2 µl of 100 mM DTT, 1 µl of 10 mM dNTPs and 200 units of Superscript™ II reverse transcriptase (Gibco/BRL) in a reaction volume 20 µl. The reaction proceeded for 1 hour at 45° C. and was terminated by incubating at 95° C. for 5 minutes. RNA was hydrolyzed with 400 µM NaOH at 65° C. for 30 minutes and neutralized with 400 µM acetic acid.

The reaction mixture was then added to 3 volumes of 6M NaI and 10 µl of treated glass beads. Beads were washed three times with 80% EtOH and nucleic acid was eluted from the beads in 45 µl of water. Nucleic acid was then precipitated and resuspended in 10 µl of water. The purified first strand cDNA was ligated to the manufacturer's provided anchor oligonucleotide (SEQ ID NO:9, 5'-CAC GAA TTC ACT ATC GAT TCT GGA ACC TTC AGA GG-3'), using T4 RNA ligase at 27° for 20 hours. One tenth of a ligation reaction was used for PCR amplification in a 50 µl reaction containing 1 µM manufacturer's anchor primer (SEQ ID NO:10, 5'-CTG GTT CGG CCC ACC TCT GAA GGT TCC AGA ATC GAT AG-3'), 1 µM mammaglobin specific primer D2Rb (SEQ ID NO:11, 5'-AAT CCG TAG TTG GTT TCT CAC C-3'), 200 µM dNTPs, 5 units of Vent™ DNA polymerase, and 1×polymerase buffer (10 mM Kcl, 20 mM TrisCl, 10 mM (NH₄)₂SO₄, 2 mM MgSO₄, 0.1% Triton X-100). The reaction was incubated at 94° for 2 minutes and then 94° for 45 seconds, 50° for 1 minute, and 72° for 90 seconds for a total of 40 times.

The two downstream mammaglobin-specific nested oligonucleotides were D2R (SEQ ID NO:4) and D2Rb (SEQ ID NO:11). An upstream mammaglobin-specific control oligonucleotide was also used as per the manufacturer's recommendations, D2F (5'-CTT TCT GCA AGA CCT TTG GC-3')(SEQ ID NO:12). All PCR amplifications were performed with Vent DNA polymerase (New England Biolabs). The amplified RACE product was digested with EcoRI and ligated into the EcoRI and SmaI sites of the plasmid vector pGEM7Z (Promega, Madison, Wis.).

All sequencing was performed using the Taq DNA polymerase thermal cycle sequencing kit as per the manufacture's protocol (Promega). Briefly the procedure used is as follows.

Ten pmol of sequence specific oligonucleotide was end labeled with 10 pmol of $^{32}$P-γ ATP (3,000 Ci/mmol and 10 mCi/ml) using T4 polynucleotide kinase in a 10 µl reaction for 30 minutes at 37° C. A polymerization reaction containing 100 ng of plasmid template, 1.5 pmol of labeled sequencing primer, and 5 units of sequencing grade Taq polymerase was created in 17 µl of the manufacturer's provided sequencing buffer. This reaction was aliquoted to a set of four reaction tubes containing manufacturer's provided mix of deoxynucleotides and either dideoxy-A, C, G, or T. The set of four tubes were incubated at 95° C. for 2 minutes and then, 94° C. for 45 seconds, 45° C. for 30 seconds, and 72° C. for 1 minute for 30 times. After reactions were completed, 3 µl of 80% formamide/ bromphenol blue dye was added to each tube. Samples were heated to 70° C. for 2 minutes and loaded on a 6% acrylamide/7.5 M urea sequencing gel and run for 2–4 hours and 60 W constant power. The gel was dried and then exposed to Kodak XAR5 Xray film for 2 to 24 hours.

The sequence thus obtained was a 403 bp fragment (SEQ ID NO:5) as shown in FIG. 2, solid bar. In earlier work the DEST002 Tag sequence was isolated (Watson and Fleming, supra). This sequence was a 206 bp fragment (SEQ ID NO:6) as shown in FIG. 2, open bar. Combining the information from these two sequences allowed the full-length 503 bp cDNA of mammaglobin to be deduced. (FIG. 2).

EXAMPLE 2

This example demonstrates that mammaglobin expression is restricted to mammary gland tumor cells and, to a lesser extent, normal mammary gland cells.

Total cellular RNA samples were isolated using the standard guanidinium isothiocyanate method and treated with RNase-free DNase (Promega). For RT/PCR analysis, 1 µg of indicated total RNA was reverse transcribed with oligo $dT_{21}$ (SEQ ID NO:13) and Superscript II reverse transcriptase (Gibco/BRL) according to the manufacture's protocol.

Two hundred ng of oligo $dT_{21}$ (SEQ ID NO:13) and 1 pg of total RNA were incubated at 65° C. for 5 minutes in a 10 µl volume. Sample was chilled on ice and added to it were 4 µl of 5×RT buffer (250 mM TrisCl pH8.3, 375 mM Kcl, 15 mM MgCl₂), 2 µl of 100 mM DTT, 1 µl of 10 mM dNTPs and 200 units of Superscript™ II reverse transcriptase (Gibco/BRL). The reaction proceeded for 1 hour at 45° C. and was terminated by incubating at 95° C. for 5 minutes.

One tenth of each RT reaction was subject to PCR analysis using the mammaglobin specific primers D2R (5'-ATA AGA AAG AGA AGG TGT GG-3') (SEQ ID NO:4) and d2102 (5'-CAG CGG CTT CCT TGA TCC TTG-3') (SEQ ID NO:3) and standard reaction conditions for 40 cycles at 94°×30 sec./55°×1 min./72°×1 min.

For Northern analysis, 20 µg of total RNA was analyzed as previously described (Watson and Fleming, supra) using the full length mammaglobin cDNA probe. Integrity and equal loading of each RNA sample was assessed by ethidium bromide staining.

As shown in FIG. 4A, the 500 bp mammaglobin message is easily detected in tumor specimen 2410 (the tissue from which this original DEST was isolated) and to a much lesser extent in normal human breast tissue but not in the immortalized breast epithelial cell line B5–589, or in human lung, placenta, uterus and ovary (FIG. 4A). Following amplification using RT/PCR analysis, mammaglobin expression was still not detected in 15 tissues surveyed (FIG. 4B). Detection of glyceraldehyde 3-phosphate dehydrogenase (GAPDH) message (FIG. 4B) and EGF receptor message (data not shown) in these reactions demonstrated that absence of expression was not due to degraded RNA or other trivial explanations. Thus the expression of mammaglobin mRNA is relatively specific for mammary tissue.

EXAMPLE 2A

This example confirms the breast specificity of mammaglobin expression in normal tissues.

The mammaglobin cDNA probe used in Example 2 was hybridized to a commercially prepared dot-blot of normalized, poly-A enriched RNAs derived from pooled populations of normal human tissues (Master Blot™, Clonetech, Palo Alto, Calif.). The dot-blot contained RNA from the following human tissues: whole brain, amygdala, caudate nucleus, cerebelum, cerebral cortex, frontal lobe, hippocamus, medulla oblongata, occipital lobe, putamen, substantia nigra, temporal lobe, thalamus, nucleus accumbeus, spinal cord, heart, aorta, skeletal muscle, colon, bladder, uterus, prostate, stomach, testis, ovary, pancreas, pituitary gland, adrenal gland, thyroid gland, salivary gland, mammary gland, kidney, liver, small intestine, spleen, thymus, peripheral leukocyte, lymph node, bone marrow, appendix, lung, trachea, placenta, fetal brain, fetal heart, fetal kidney, fetal liver, fetal spleen, fetal thymus, and fetal lung.

The mammaglobin cDNA probe was radiolabled with $^{32}$P-α-dCTP (10 mCi/ml; >3000 Ci/mmol) and the Rediprime labeling kit (Amersham, Arlington Heights, Ill.) following the supplier's protocol. The dot blot was hybridized with 1×10$^6$ CPM/ml of the mammaglobin cDNA probe at 60° C. for 16 hours using Rapid-Hyb hybridization buffer (Amersham, Arlington Heights, Ill.). Filters were then washed twice at room temperature for 15 min. in 2×SSC/0.1% SDS, and washed twice again at 60° C. for one hour in 0.2×SSC/0.1% SDS. Washed filters were exposed to XAR5 film (Eastman-Kodak, Rochester, N.Y.) with phosphor enhancing screens for 72 hours.

Mammaglobin mRNA was only detected in RNA from the mammary gland (data not shown). The lack of detectable mammaglobin mRNA in normal salivary gland and prostate indicates that mammaglobin expression is not associated with the apocrine phenotype as opposed to the apocrine cell specificity of GCDP15, which has been used as a breast-specific marker. Wick et al., *Hum Pathol* 20:281–287, 1989; Raab et al., *Am J Clin Pathol* 100:27–35, 1993. These results suggest potential advantages for using mammaglobin gene expression as a very specific marker for breast cancer.

EXAMPLE 3

This example demonstrates that the mammaglobin cDNA encodes a translatable nucleotide sequence which results in a protein product of appropriately predicted molecular mass. In vitro translations were performed using the TNT™ rabbit reticulocyte translation kit with T7 RNA polymerase (Promega) and $^{35}$S-Methionine (>1000 Ci/mmol; 10 mCi/ml, Amersham) according to the manufacturer's protocol.

To 25 µl of TNT™ rabbit reticulocyte lystae was added 2 µl of manufacturer's prepared reaction buffer, T7 RNA polymerase, 20 µM amino acid mixture minus methionine, 40 µCi$^{35}$S-methionine (1,000 Ci/mmol and 10 mCi/ml), 40 units ribonuclease inhibitor, 1 µg of mammaglobin/pGEM7 plasmid, and sufficient DEPC treated water to create a final reaction volume of 50 µl. This reaction was incubated at 30° C. for 60 minutes. 5 µl of this reaction was removed into 20 µl of SDS gel buffer, boiled for 2 minutes, and loaded on a 17.5% SDS-polyacrylamide gel.

Rabbit reticulocyte lysate programmed with mammaglobin cDNA produced a 6 kD protein while that programmed with no cDNA did not produce any protein product.

EXAMPLE 4

This example illustrates the prevalence of overexpression of mammaglobin in primary breast carcinoma.

Figure 6:
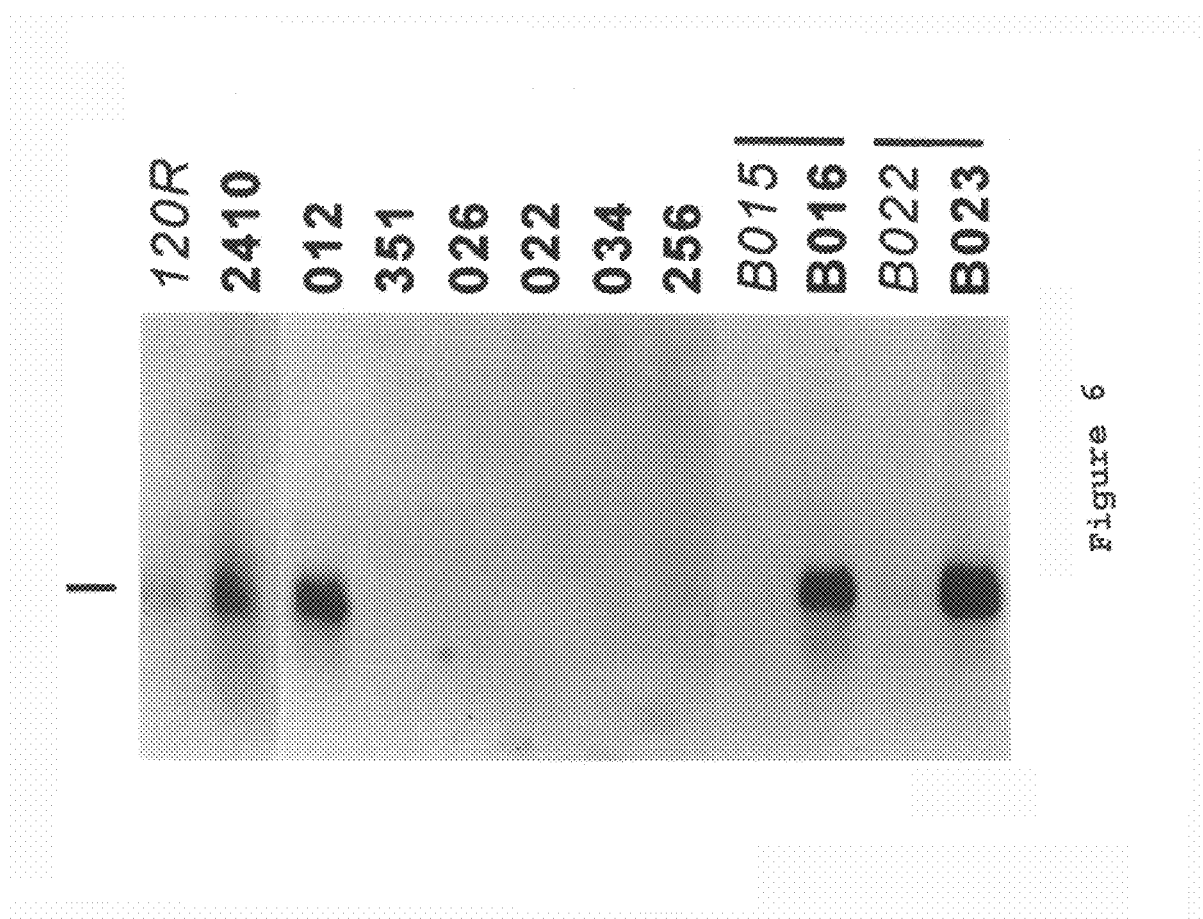
FIG. 6 illustrates Northern blot hybridization with the cDNA encoding mammaglobin showing detection of mRNA in tumor 2410, in tumors from three of eight other patients (shown in bold), and to a lesser extent, in normal breast tissue (shown in italics), and comparing in two cases (the four lanes on the right) mammaglobin mRNA expression in tumor tissue and patient matched normal tissue.

To determine the frequency of mammaglobin overexpression in breast carcinomas, we examined a panel of fifteen, stage I primary breast carcinomas of differing histological types using Northern blot hybridization with the mammaglobin cDNA probe. Patient-matched normal breast tissues samples were also compared in tissues from two patients (FIG. 6). The 500 bp mammaglobin mRNA was detected in normal breast tissue and tumor 2410 and in three other tumors, two of which when tested demonstrated little or no expression in patient-matched normal tissue (BO15 v. BO16; B022 v. B023) (FIG. 6). In all, 4 of 15 (27%) of tumors examined overexpressed mammaglobin mRNA.

These data indicate that overexpression of mammaglobin is not unique to a single tumor specimen and is, in fact, relatively frequent among primary breast tumors. Furthermore, the fact that all tumors examined were stage I suggests that this dysregulation occurs relatively early in the progression of breast neoplasia.

EXAMPLE 5

The following example illustrates the detection of the mammaglobin protein using an anti-mammaglobin polyclonal antibody.

The anti-mammaglobin polyclonal antibody was prepared by coupling a peptide corresponding to the 16 C-terminal amino acids predicted from mammaglobin cDNA (Glu-Val-Phe-Met-Gln-Leu-Ile-Tyr-Asp-Ser-Ser-Leu-Cys-Asp-Leu-Phe, SEQ ID NO:14) to Keyhole Lymphet Hemocyanin and injecting into rabbits with Freund's adjuvant. The inoculated rabbits were boosted at three week intervals and on week 12, the rabbits were bled and the sera was assayed for its ability to detect mammaglobin in serum-free conditioned medium from cultures of the breast tumor cell lines MDA-MB-415 and MCF-7. MDA-MB-415 had been identified earlier as a cell line that overexpresses the mammaglobin message and MCF-7 had been identified as a cell line that produces no detectable mammaglobin mRNA.

The conditioned media was harvested from a 24 hr. culture and resolved on a 12% SDS acrylamide gel under reducing conditions (i.e., the sample was boiled in buffer containing dithiothreitol (DTT) and 2-mercaptoethanol (BME) to reduce disulfide bonds), blotted onto a Nytran filter, and analyzed by standard Western blot protocols using the above described antibody to the C-terminal peptide as the primary antibody in this assay. After primary antibody binding, the blot was washed and secondary antibody (goat anti-rabbit) was added. Mammaglobin-antibody complexes were visualized by enzyme-linked chemiluminescence (ECL Western Blotting Detecting Reagent, Amersham, Arlington Heights, Ill.).

The anti-mammaglobin polyclonal antibody detected a band with an apparent molecular weight of approximately 21 kD in the conditioned media of the MDA-MB-415 cell culture (data not shown). No bands were detected in the conditioned medium of the MCF-7 cell culture (data not shown). Thus, consistent with the mRNA data, MDA-MB-415 cells secrete mammaglobin protein but MCF-7 cells do not. The apparent molecular weight of the mammaglobin secreted into the MDA-MB-415 culture media is greater than the 10.5 kDa molecular weight calculated from the predicted amino acid sequence of SEQ ID NO:2. Since almost all secreted proteins are glycosylated, the cytosol of MDA-MB-415 cells was analyzed with the anti-mammaglobin polyclonal antibody to see if any precursor forms of secreted mammaglobin could be detected.

MDA-MG-415 cells were grown for 24 hours in serum-free media, the culture media was collected, spun, and the resulting supernatant was collected. The attached cells were washed with phosphate buffered saline (PBS) and lysed with 1×Laemmli sample buffer (2% SDS, 10% glycerol, 100 mM DTT, 60 mM Tris, pH 6.8, 0.001% Bromophenol Blue). The lysis mixture was boiled for 5 minutes and then spun at 10,000 g for 5 minutes to pellet the cell debris. The cell lysate was transferred to a new tube and used for Western blot analysis as described below.

The culture supernatant and cell lysate were run on a 12% SDS acrylamide gel under reducing conditions (i.e., samples boiled in buffer containing DTT and BME) and blotted onto a PVDF membrane using standard techniques. The blot was probed with the polyclonal antibody to the C-terminal peptide in the presence and absence of the competing peptide used to generate the antibody.

Figure 7:
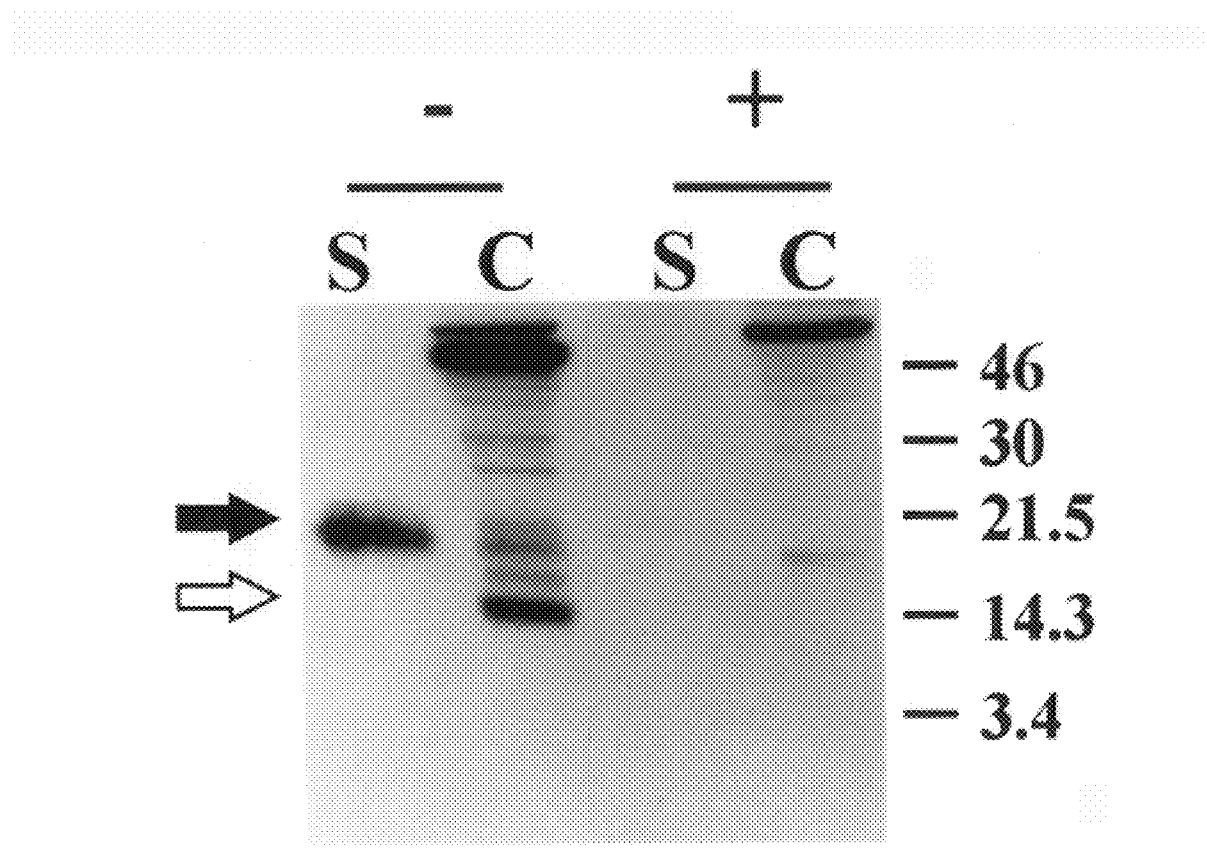
FIG. 7 illustrates the Western blot analysis using polyclonal antibody to the mammaglobin C-terminus (SEQ ID NO:14) of the conditioned medium (S) and cell lysate (C) from MDA-MB-415 breast tumor cells in the absence (−) and presence (+) of the immunizing peptide showing detection of the precursor and secreted forms of mammaglobin protein in the cell medium and cell lysate, respectively.

Visualization of mammaglobin-antibody complexes were as discussed above. As seen in FIG. 7, in the absence of competing peptide (−), the conditioned media (S) has the 21 kD band representative of the secreted mammaglobin protein. The cell lysate (C) showed a prominent band at approximately 14 kD, and several higher molecular weight bands, including one at approximately 21 kD. When the Western blot is performed in the presence of the competing peptide (+), the secreted form and intracellular forms of mammaglobin are not visualized, indicating that these proteins contain the peptide to which the antibody was synthesized.

The 14 kD band detected only in the cell lysate likely represents a precursor, or unprocessed, form of mammaglobin. Since the predicted amino acid sequence for mammaglobin has the consensus N-glycosylation site, Asn-X-Thr, located at residues 53–55 and at residues 68–70 of SEQ ID NO:2, the observed, secreted 21 kD form likely represents some glycosylated form of the protein.

This hypothesis was tested by culturing MDA-MB-415 cells in the presence and absence of tunicamycin, a drug that blocks N-linked glycosylation of eukaryotic proteins. Tunicamycin was added to one of two identical cultures at 1 ug/ml and both cultures were incubated overnight for more hours. The culture media and cell lysate from the treated and control cultures were prepared and analyzed by Western blot analysis as described above.

Figure 8:
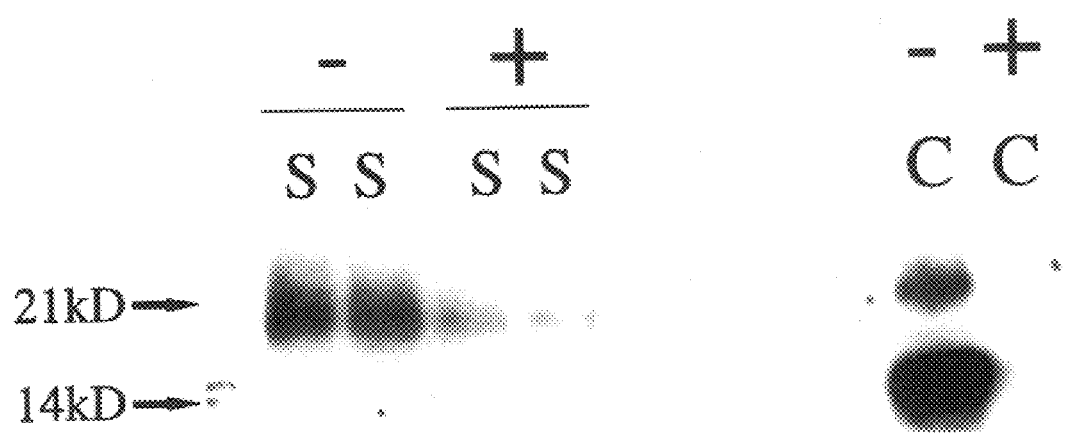
FIG. 8 illustrates the Western blot analysis using the anti-mammaglobin polyclonal antibody of the conditioned medium (S) and cell lysate (C) from MDA-MB-415 breast tumor cells grown in the absence (−) and presence (+) of tunicamycin, which blocks glycosylation, showing the lack of detectable mammaglobin protein in the lysate or medium of cells in which N-linked glycosylation is inhibited.

As shown in FIG. 8, media from cultures (S) treated with tunicamycin (+) lack detectable levels of secreted mammaglobin, suggesting that secreted mammaglobin is glycosylated. Surprisingly, the cell cytosol form of mammaglobin (14 kD) was also not detectable in lysates of MDA-MB-415 cells treated with tunicamycin (far right lane). We hypothesize that blocking early glycosylation events with tunicamycin leads to instability and degradation of precursor forms of mammaglobin, thus explaining the lack of detectable 14 kD protein in the cytosol of tunicamycin-treated cells.

Figure 9:
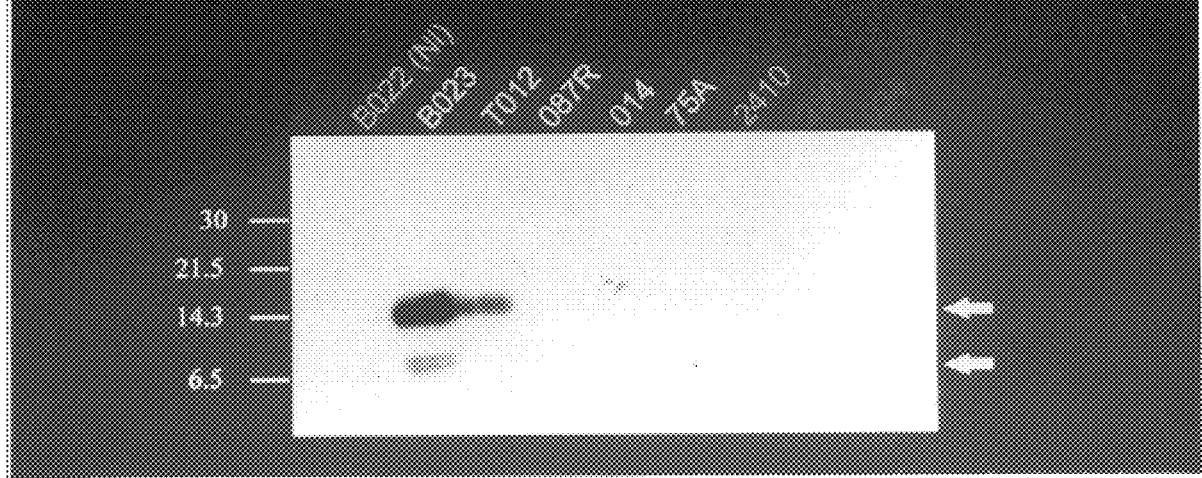
FIG. 9 illustrates the Western blot analysis of cell lysates from human breast tumor cells showing detection of the precursor mammaglobin protein using the anti-mammaglobin polyclonal antibody and goat anti-rabbit antibody visualized by enzyme-linked chemiluminescence.

The polyclonal antibody to the C-terminal peptide of mammaglobin has also detected the 14 kDa precursor form of mammaglobin in cell lysates from primary human breast tumor specimens. As seen in FIG. 9, the precursor form of mammaglobin is present in tumor specimen B023, but is undetectable in a normal breast tissue sample from the same patient (BO22). Interestingly, some tumor samples that express the mammaglobin transcript (i.e., 087R, 014, 75A and 2410) do not contain detectable levels of mammaglobin protein as assayed by Western blot analysis. One hypothesis consistent with these data is that mammaglobin expression is differentially regulated at the levels of transcription and translation and that this differential regulation is determined the developmental stage of the tumor.

The anti-mammaglobin polyclonal antibody has also been used to look for secreted mammaglobin in breast secretions from proliferating mammary gland. Colostrum or mature milk fluid (500 ul samples) was collected by manual expression from a pregnant woman during the first and third trimester, at birth, and at day 3, 14, and 21 post-partum. The samples were diluted with an equal volume of 2×laemmli sample buffer (4% SDS, 20% glycerol, 200 mM DTT, 120 mM Tris, pH 6.8, 0.002% Bromophenol Blue). The diluted samples were boiled for 5 min. and then spun at 10,000 g for 5 min. at 4° C. to pellet cell debris. The denatured samples were transferred to a new tube and stored at −20° C. prior to Western blot analysis as described above.

Figure 10:
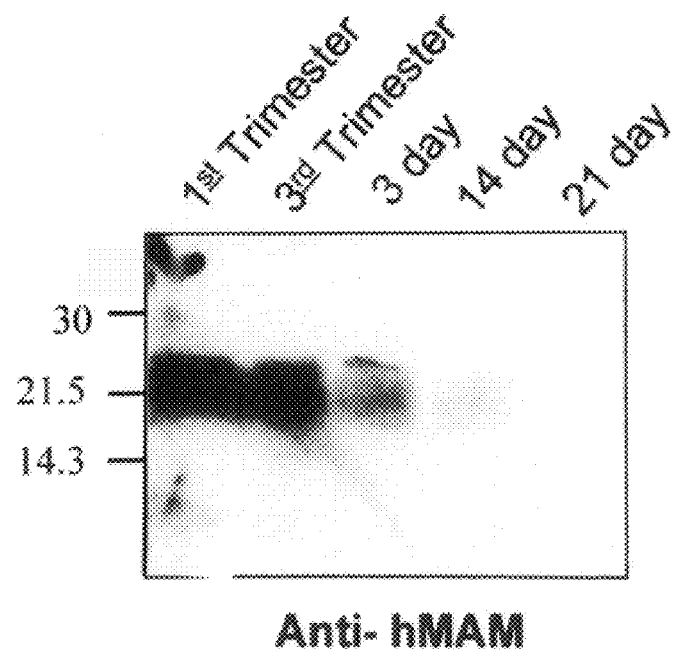
FIG. 10 illustrates the Western blot analysis using the anti-mammaglobin polyclonal antibody of fluid secretions from human breast during pregnancy and postpartum showing detection of the secreted mammaglobin protein in proliferating mammary gland.

As shown in FIG. 10, the antibody detected the 21 kD secreted mammaglobin in breast secretions sampled during pregnancy, a period of high proliferation of breast epithelial cells. However, at the onset of lactation, a stage of breast epithelial differentiation, mammaglobin levels decreased significantly by 3 days post partum and was no longer observed at 14 days post-partum. These results indicate that secreted mammaglobin is associated with proliferating breast epithelial cells, an observation consistent with the detection of secreted mammaglobin in human breast cancer.

Figure 11A:
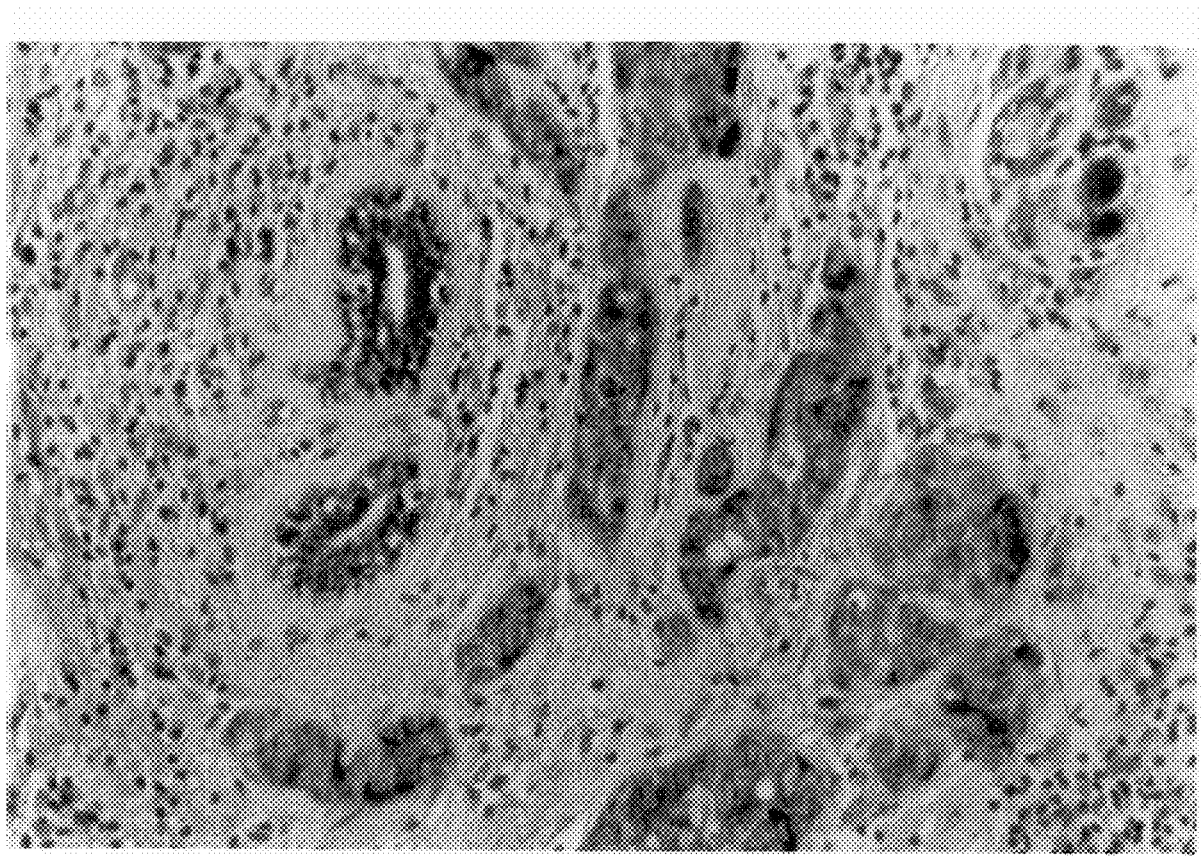
FIG. 11A illustrates in color a paraffin-fixed section of breast cancer cells from a patient specimen immunohistochemically stained using the anti-mammaglobin polyclonal antibody and goat anti-rabbit antibody tagged with horseradish peroxidase and DAB as substrate showing a brown staining of cells expressing the mammaglobin protein.
Figure 11B:
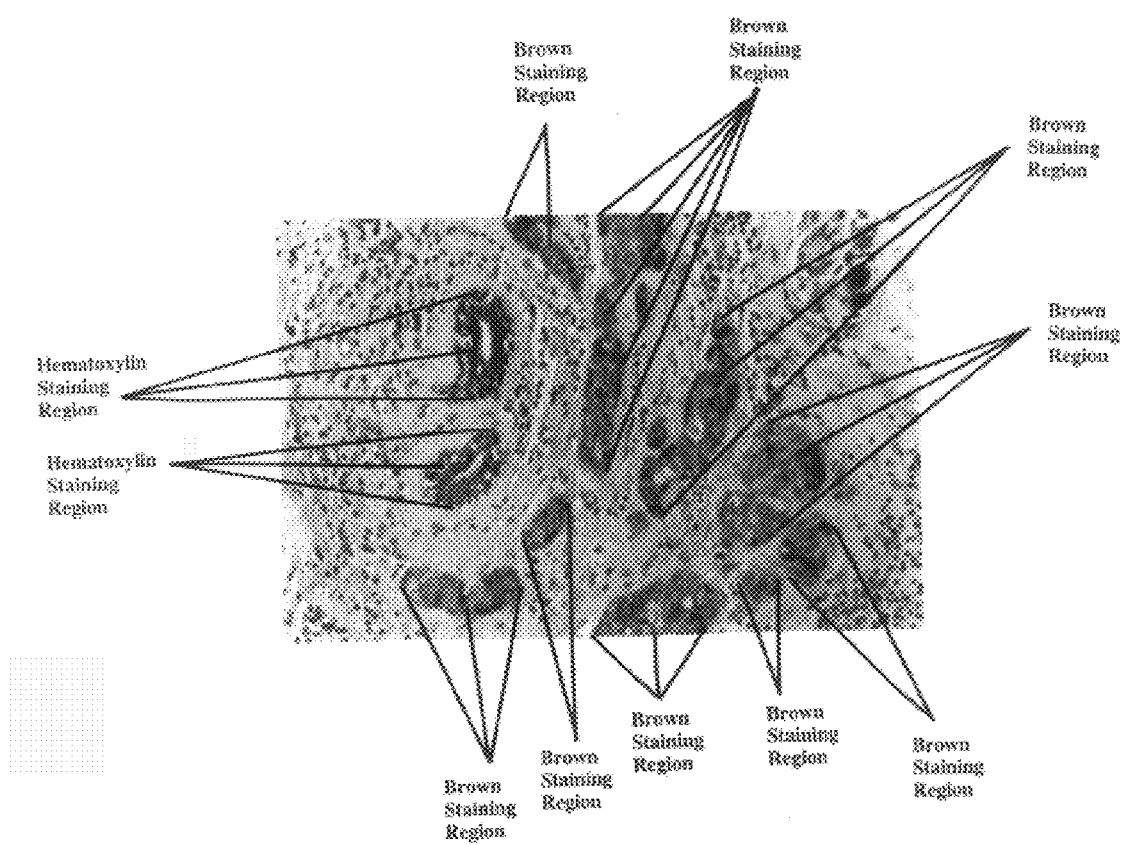
FIG. 11B illustrates in black and white a paraffin-fixed section of breast cancer cell from a patient specimen immunohistochemically stained using the anti-mammaglobin polyclonal antibody and goat anti-rabbit antibody tagged with horseradish peroxidase and DAB as substrate wherein the brown staining of cells expressing the mammaglobin protein is indicated.

Reactivity with the antibody to the manunaglobin peptide has also been shown for breast tumor cells by immunohistochemical staining of paraffin-fixed sections of a breast cancer patient specimen (FIG. 11). The immunohistochemical staining was performed using the antibody to the mammaglobin peptide as the primary antibody and then detecting the mammaglobin-antibody complex using goat anti-rabbit antibody tagged with horseradish peroxidase and 3,3' diamino benzene tetrahydrochloride (DAB) as substrate. Cells expressing the mammaglobin protein showed a brown staining.

From the results, it is believed that the mammaglobin protein is synthesized as a precursor protein and post-translational modifications such as N-linked glycosylation increase its apparent molecular weight prior to secretion; that the stability of precursor forms of mammoglobin is dependent on N-linked glycoslyation and that mammaglobin protein is secreted by proliferating breast tumor cells.

EXAMPLE 6

This example illustrates detection of mammaglobin protein in primary breast tumors by immunohistochemical analysis using the anti-mammaglobin rabbit polyclonal antibody described in Example 5.

One hundred archived breast tumor specimens were chosen at random from the Vanderbilt University Department of Pathology and the Washington University Cancer Center Tumor Repository. Formalin-fixed, paraffin-embedded tissues were cut at 5 µm, mounted on charged slides, and dried.

For immunohistochemical analysis, slides were deparaffinized and rehydrated in graded solutions of ethanol and distilled water. Tissue sections were preincubated with normal goat serum (Vector Laboratories, Burlingame, Calif.) at a 1:100 dilution in 3% bovine serum albumin (BSA)/ phosphate buffered saline (PBS) and then with the anti-mammaglobin rabbit polyclonal antibody at a 1:1000 dilution for 1 hour at room temperature. After several rinses in PBS, sections were incubated in a solution of normal goat serum (1:1000), 3% BSA, and 6 µg/ml of biotinylated goat anti-rabbit IgG (Vector Laboratories, Burlingame, Calif.) in PBS for 1 hour. The secondary antibody solution was rinsed four times in PBS and tissues were then incubated with a 1:1000 dilution of streptavidin peroxidase (Boehringer Mannheim, Indianapolis, Ind.) also in a solution of 3% BSA/PBS. After a 30 minute incubation, slides were again rinsed four times in PBS and exposed to chromagen solution containing 1 mg/ml 3,3'-diaminobenzidine tetrahydrochloride (Dako, Carpinteria, Calif.) and 0.02% hydrogen peroxide for 3 minutes. Slides were rinsed briefly in deionized water, counterstained with Harris' hemotoxylin, and mounted under coverslips.

For negative controls, tissue sections were processed identically except a 1:500 dilution of pre-immune rabbit serum was substituted for the anti-mammaglobin antiserum. Alternatively, for peptide competition experiments, mammaglobin antiserum was first incubated with the 16 residue mammaglobin peptide at a concentration of 100 µg/ml in 3% BSA/PBS for 1 hour at room temperature and then applied to tissue sections.

Figure 12:
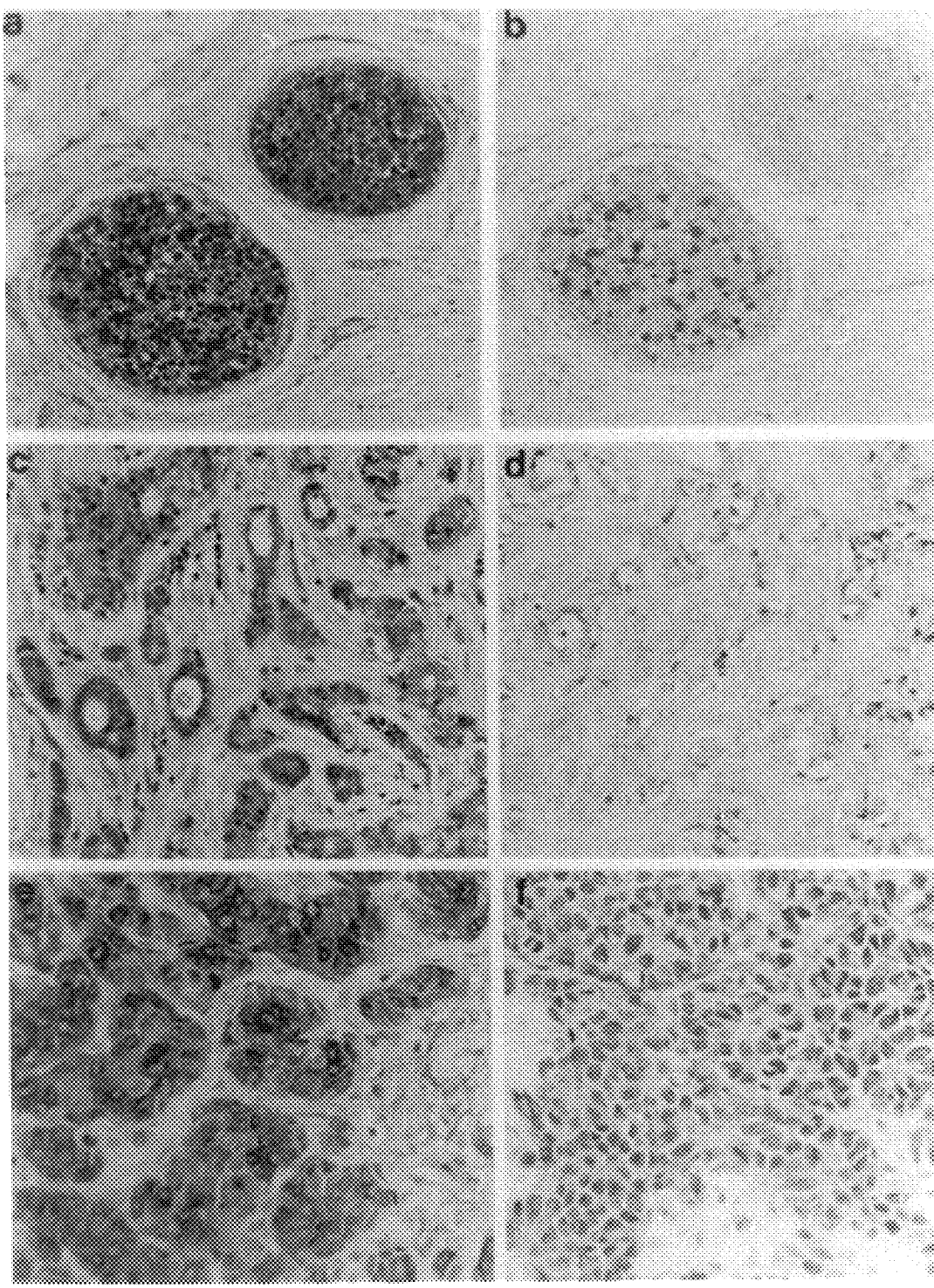
FIG. 12 illustrates mammaglobin immunoreactivity in tissue sections from the same specimens of (FIGS. 12A, 12B) pure ductal carcinoma in situ (DCIS), (FIGS. 12C, 12D) well differentiated ductal carcinoma, and (FIGS. 12E, 12F) poorly differentiated ductal carcinoma which were immunohistochemically stained with (FIGS. 12A, 12C, 12E) mammaglobin antiserum or (FIGS. 12B, 12D, 12F) pre-immune antiserum.

Immunopositivity was scored as 0: no staining, 1: weak and sporadic staining in less than 50% of tumor cells, 2: weak staining in greater than 50% of tumor cells, 3: strong, diffuse cytoplasmic staining in less than 50% of tumor cells, 4: strong, diffuse cytoplasmic staining in greater than 50% of tumor cells. Only sections scoring 3 or 4 were considered mammaglobin "positive". The scoring results are shown in Table I below and representative staining patterns for three tumor types are shown in FIG. 12.

TABLE 1

Mammaglobin immunoreactive staining in human breast cancer

| Tumor Type[1] | Staining Score[2] | | | | | Total |
|---|---|---|---|---|---|---|
| | 4 | 3 | 2 | 1 | 0 | |
| Lobular | 0 | 1 (33%) | 1 (33%) | 0 | 1 (33%) | 3 |
| Well Differentiated | 11 (78%) | 0 | 1 (7%) | 0 | 2 (14%) | 14 |
| Moderately Differentiated | 28 (67%) | 5 (12%) | 3 (7%) | 2 (5%) | 4 (10%) | 42 |
| Poorly Differentiated | 24 (63%) | 9 (24%) | 2 (5%) | 0 | 3 (8%) | 38 |
| DCIS | 1 (33%) | 2 (67%) | 0 | 0 | 0 | 3 |
| Total | 64 | 17 | 7 | 2 | 10 | 100 |

[1]Except for lobular and ductal carcinoma in situ (DCIS), all speciments are invasive cancers.
[2]The degree of immunopositive staining of breast tumor tissue sections with anti-mammaglobin antibodiy was rated as 0: No staining, 1: Weak staining in <50% of tumor cells, 2: Weak staining in >50% of tumor cells, 3: Strong, cytoplasmic staining in <50% of tumor cells, 4: Strong, cytoplasmic staining in >50% of tumor cells. For purposes of discussion, mammaglobin 'positive' tumors are those that scored 3 or 4.

Overall, 80% of ductal carcinomas examined demonstrated strong global or focal cell staining for mammaglobin protein. Interestingly, staining was equally frequent among well differentiated (78%), moderately differentiated (67%), and poorly differentiated (63%) tumors (Table 1, FIG. 12). Strong staining was also seen in 3/3 cases of pure ductal carcinoma in situ (DCIS) (FIG. 12A). The cellular staining pattern of mammaglobin was predominantly diffuse and cytoplasmic, although some cells also demonstrated localized staining adjacent to the nucleus. In normal breast tissue, mammaglobin staining was observed only in rare epithelial cells within small ducts and lobules.

However, as has been observed with other secretory proteins, increased expression of mammaglobin coincided with features of apocrine metaplasia. In benign breast tissue with metaplastic apocrine epithelium, mammaglobin immunoreactivity was present both within the epithelium and in the apocrine cyst fluid. The specificity of these patterns of positive staining were documented by the lack of signal from identical specimens incubated with either pre-immune rabbit serum (FIGS. 12B, 12D, 12F) or anti-mammaglobin antiserum preincubated with competing C-terminal peptide (data not shown).

However, mammaglobin expression was not detected in other apocrine tissues such as the normal prostate and salivary gland. Furthermore, breast tumor cells with both apocrine and non-apocrine features express mammaglobin with roughly equal frequency and intensity. There is also apparently no correlation between mammaglobin expression and tumor grade. Therefore, it is believed that mammaglobin expression is a marker of a unique breast tumor phenotype and may be useful in conjunction with other established markers to further define breast tumors at the molecular level.

The results described in Examples 5 and 6 indicate that detection of a mammaglobin protein will be applicable in cancer diagnostics using the mammaglobin protein as a breast tumor marker, in assessing breast tumor relapse, in monitoring autologous bone marrow/stem cell transplants for contaminating tumor cells, and in targeting breast tumor cells for therapeutic intervention via antibody-mediated complexes. A purified and isolated mammaglobin polypeptide is useful for generating antibodies against breast tumors and in the development of other tumor-specific immunotherapy regimens.

EXAMPLE 7

This Example illustrates the detection of mammaglobin mRNA in lymph nodes.

Mammaglobin's expression in a large percentage of primary breast tumors and its absence in lymphoid tissues suggested that it would be a sensitive and specific marker for detecting metastatic breast tumor cells within lymph nodes. To test this idea, mammaglobin mRNA expression was examined in lymph nodes containing either histologically documented breast metastases or other non-mammary metastatic tumors. Expression of mammaglobin was also compared to that of keratin 19, an epithelial cell-specific marker, to normalize mammaglobin signals to the total number of malignant epithelial cells present in each lymph node sample.

Anonymized lymph node specimens containing metastatic lesions were obtained from the Cooperative Human Tissue Network (LiVolsi et al., *Cancer* 71:1891–1894, 1993) and the Washington University Cancer Center Tumor Repository. Tissue specimens were pulverized and homogenized in Trizol reagent (Life Technologies, Rockville, Md.) at a concentration of 100 mg of tissue per ml of reagent. RNA isolation was performed exactly as recommended in the manufacturer's protocol and the resulting RNA was resuspended at a concentration of 2 µg/µl in RNase-free water. Twenty µg of each RNA was subjected to formaldehyde agarose gel electrophoresis and transferred to Nytran Plus membranes (Schleicher &. Schuell, Keene, N.H.) using 10×SSC buffer and standard methodology.

To generate a mammaglobin hybridization probe, the mammaglobin cDNA used in Example 2 was radiolabled with $^{32}$P-α-dCTP (10 mCi/ml; >3000 Ci/mmol) and the Rediprime labeling kit (Amersham, Arlington Heights, Ill.) following the supplier's protocol.

A keratin 19 hybridization probe was constructed as follows. Forward (5'-CGCGGATCCAGGATTGTCCTGCAGAT-3')(SEQ ID NO:18) and reverse (5'-CCGGAATTCCCATCCCTCTACCCAGA-3')(SEQ ID NO:19) keratin 19 specific oligonucleotide sequences were used in a standard PCR amplification reaction of normal human breast cDNA to generate a k19 cDNA fragment encompassing the coding region from nucleotide 477 to nucleotide 1298 (Stasiak, P. C. and Lane, E. B., *Nucleic Acids Res* 15:10058, 1987.). This fragment was digested to generate EcoRI and BamHI ends, cloned into the corresponding sites of the pGEM3Z vector (Promega, Madison, Wis.) and sequenced to confirm identity. The cloned, 821 bp k19 cDNA fragment was radiolabled as described above.

The Northern blot filters were first hybridized with 1×10$^6$ CPM/ml of the mammaglobin hybridization probe at 60° C. for 16 hours using Rapid-Hyb hybridization buffer (Amersham, Arlington Heights, Ill.). Filters were then washed twice at room temperature for 15 min. in 2×SSC/0.1% SDS, and washed twice again at 60° C. for one hour in 0.2×SSC/0.1% SDS. Washed filters were exposed to XAR5 film (Eastman-Kodak, Rochester, N.Y.) with phosphor enhancing screens for 72 hours. The filters were allowed to decay for several half-lives and then rehybridized with 1×10$^6$ CPM/ml of the keratin 19 hybridization probe without pretreatment of the filters. Equal counts and specific activities of mammaglobin and keratin 19 cDNA probes were used and each hybridization was exposed to film under equivalent conditions.

Figure 13:
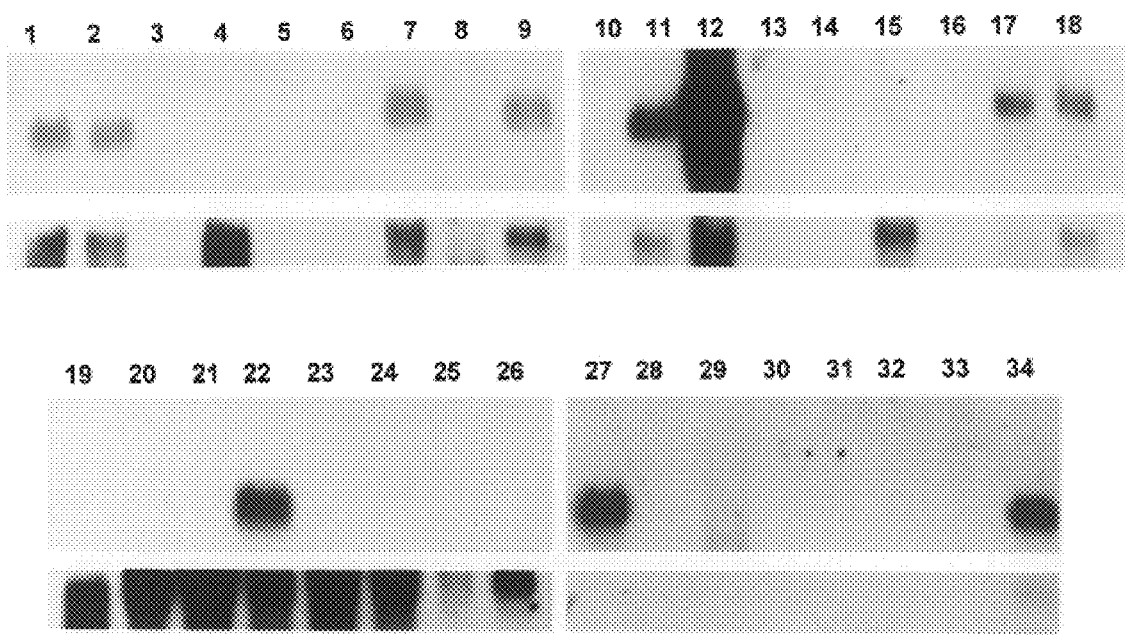

The results of this survey are shown in FIG. 13. Among 21 cases of lymph nodes containing histologically documented metastatic breast cancer (lanes 1–20, 27), mammaglobin expression could be detected in 9 of the cases (43%) (lanes 1, 2, 7, 9, 11, 12, 17, 18, and 27). However, in 6 of the 21 cases, neither mammaglobin nor keratin 19 mRNA could be detected (lanes 3, 5, 6, 10 13, 14, 16, 19 and 20) suggesting that the lymph node samples from these cases may have contained too few tumor cells to be assayed by this method. When these six cases were excluded, 60% (9/15) of cases contained detectable mammaglobin mRNA. In at least one case, mammaglobin expression was detected in the absence of keratin 19 expression (lane 27), suggesting that mammaglobin may be a more sensitive marker in a subset of tumors. Furthermore, keratin 19 was ubiquitously expressed in many cases of non-mammary metastases, e.g., lymph nodes with laryngeal and billary tumor involvement (lanes 21–26), while mammaglobin expression was detected in only one case of a non-mammary metastatic lesion (lane 22). This case was an inguinal lymph node containing poorly-differentiated adenocarcinoma of unknown origin. Since a previous history of endometrial cancer was documented, this lesion was presumed to be a metastatic recurrence of the disease. We have recently detected mammaglobin expression in several primary endometrial cancers (data not shown), thus confirming the idea that mammaglobin, while not expressed in normal endometrial tissue, is expressed in a subset of endometrial as well as breast cancers. In all cases of lymph nodes without metastatic disease (lanes 29–33), both keratin 19 and mammaglobin expression were undetectable. As expected mammaglobin mRNA was detected in RNA isolated from normal breast tissue (lane 34).

EXAMPLE 8

This example illustrates detection of mammaglobin mRNA in peripheral blood stem cell (PBSC) collections as a marker for circulating breast tumor cells.

Aliquots of ~1×10$^6$ peripheral leukocytes were obtained from leukopheresis products of 15 patients undergoing high dose chemotherapy and autologous stem cell transplant for metastatic breast cancer. For positive controls, 10$^1$ mammaglobin-expressing MDA-MB 175 human breast tumor cells (Watson et al., *Cancer Res* 56:860–865, 1996.) were mixed with 10$^6$ human OM431 melanoma cells to yield a 1:10$^5$ breast cancer cell dilution. A pure population of OM431 cells was used as a negative control. Frozen cell aliquots were immediately lysed in 1 ml of Trizol reagent (Life Technologies, Rockville, Md.) and total RNA was prepared as per the supplier's protocol. RNA integrity and concentration was assessed by agarose gel electrophoresis.

Approximately one microgram of total RNA was converted to first-strand cDNA using a $T_{11-17}$ primer and the Superscript II preamplification system (Life Technologies, Rockville, Md.) as per the supplier's protocol. After treatment with and inactivation of RNase H, samples were diluted two-fold with nuclease-free water and stored at −20° C. To assess the integrity of synthesized cDNA, 10% of the cDNA was subjected to a 50 µl PCR reaction containing a final concentration of 1×Taq DNA polymerase buffer, 1.5 mM MgCl$_2$, 200 µM dNTPs, 0.6 µM Glyceraldehyde-3-Phosphate Dehydrogenase (GAPDH) forward amplification primer (5'-CCACCCATGGCAAATTCCATGGCA-3')(SEQ ID NO:20), 0.6 µm GAPDH reverse amplification primer (5'-TCTAGACGGCAGGTCAGGTCCACC-3')(SEQ ID NO:21), and 2.5 units Taq DNA polymerase (Life Technologies, Rockville, Md.). Reactions were heated to 94° C. for 1 minute and then subjected to 30 cycles of 94° C. for 30 seconds, 58° C. for 60 seconds, and 72° C. for 45 seconds. PCR products were analyzed on a 2% agarose gel and a single, uniformly intense fragment of 599 nt. indicated that each cDNA synthesis reaction had been successful. An additional 10% of the cDNA reaction was then subjected to a second 50 μl PCR reaction containing a final concentration of 1×Taq DNA polymerase buffer, 1.5 mM $MgCl_2$, 200 μM dNTPs, 0.6 μM mammaglobin forward amplification primer (5'-AGCACTGCTACGCAGGCTCT-3')(SEQ ID NO:16), 0.6 μm mammaglobin reverse amplification primer (5'-ATAAGAAAGAGAAGGTGTGG-3')(SEQ ID NO:4), and 2.5 units Taq DNA polymerase (Life Technologies, Rockville, Md.). Reactions were heated to 94° C. for 1 minute and then subjected to 45 cycles of 94° C. for 30 seconds, 58° C. for 60 seconds, and 72° C. for 30 seconds. Amplification products were delivered to an alternate laboratory site, electrophoresed on a 2% agarose gel, and subjected to Southern blot analysis using 0.2 μm Nytran Plus membrane and the supplier's protocol for the neutral transfer method (Schleicher & Schuell, Keene, N.H.). The resulting filter was hybridized with $1 \times 10^6$ CPM/ml of mammaglobin cDNA probe and washed as described above.

Figure 14:
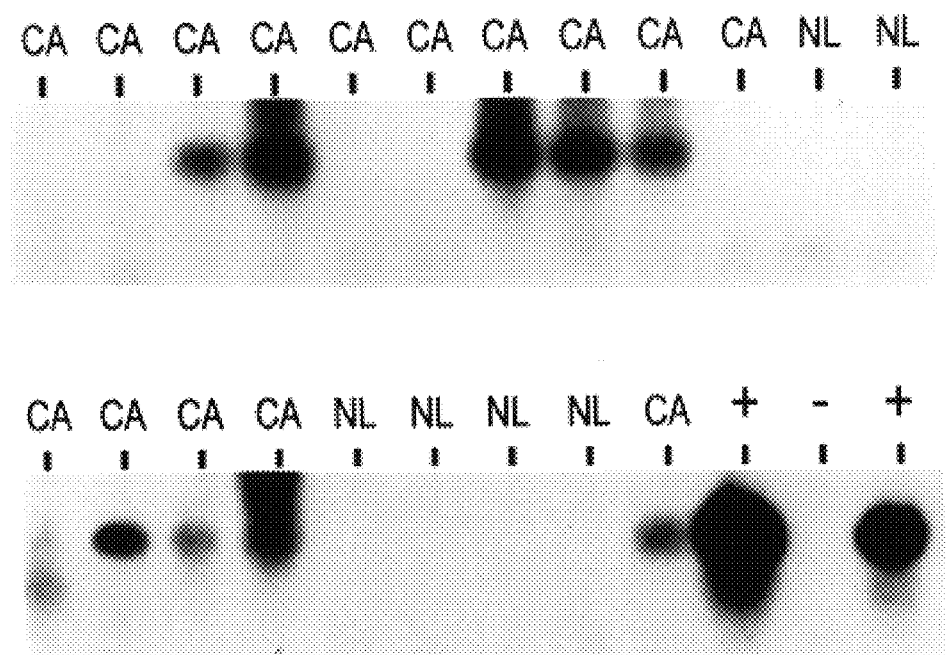
FIG. 14 shows a photograph of a Southern blot of RT-PCR products of RNA from patients with metastatic breast cancer (CA) or normal donors (NL) obtained from peripheral stem cell collections and probed with the mammaglobin cDNA probe.

The results of this assay are shown in FIG. 14. Of fifteen breast cancer cases (CA), nine patients (60%) yielded detectable mammaglobin mRNA from their PBSCs, suggesting that the collected products contained contaminating breast tumor cells. In the remaining six cases, because the primary tumors were not examined for mammaglobin expression, it was not known whether the lack of signal for the PBSCs represented a lack of mammaglobin-expressing tumor cells, a true absence of tumor cells, or assay insensitivity. In no cases of collections from healthy donors (NL) was mammaglobin mRNA detected. Based on the robust hybridization signal obtained from duplicated positive controls (+) containing $1:10^5$ breast tumor cells, the limit of detection for the current assay format is probably well below $1:10^6$ cells. The frequency of detection and high specificity of this assay suggest that it may be a useful tool for studying the prognostic significance of occult circulating tumor cells in larger, prospective studies. For example, mammaglobin expression may be useful to evaluate tumor contamination of peripheral stem cell products after cytokine priming (Passos-Coelho et al., *J. Clin. Oncol.* 14:2569–2575, 1996) or tumor cell purging protocols (Passos-Coelho et al., *Cancer Res.* 54:2366–2371, 1994).

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

All references cited in this specification, including patents and patent applications, are hereby incorporated by reference. The discussion of references herein is intended merely to summarize the assertions made by their authors and no admission is made that any reference constitutes prior art. Applicants reserve the right to challenge the accuracy and pertinency of the cited references.

What is claimed is:

1. A method for detecting the presence of breast cancer in a patient which comprises detecting the presence of mammaglobin polypeptide in a sample from the patient by reacting the mammaglobin polypeptide with a purified antibody and detecting a binding of the mammaglobin polypeptide with the antibody, wherein the antibody is specific for a mammaglobin epitope comprising at least five amino acids of SEQ ID NO:14 and wherein an elevated expression of said mammaglobin polypeptide above the expression level in a normal sample indicates the presence of breast cancer.

2. The method of claim 1, wherein said mammaglobin polypeptide comprises SEQ ID NO:17.

3. The method of claim 2 wherein the purified antibody is a polyclonal antibody.

4. The method of claim 2 wherein the purified antibody is a monoclonal antibody.

5. The method of claim 1 wherein the sample comprises breast tumor tissue.

6. A kit for detecting the presence of breast cancer cells in a sample which comprises a purified antibody packaged in a container, wherein said antibody is specific for a mammaglobin epitope comprising at least five amino acids of SEQ ID NO:14 and wherein said antibody reacts with a mammaglobin polypeptide comprising SEQ ID NO:17.

7. The method of claim 1 wherein the sample is breast tissue.

* * * * *

SEQUENCE LISTING

<160> NUMBER OF SEQ ID NOS: 21

<210> SEQ ID NO 1
<211> LENGTH: 503
<212> TYPE: DNA
<213> ORGANISM: Homo sapiens

<400> SEQUENCE: 1

```
gacagcggct tccttgatcc ttgccacccg cgactgaaca ccgacagcag cagcctcacc      60
atgaagttgc tgatggtcct catgctggcg gccctctccc agcactgcta cgcaggctct     120
ggctgcccct tattggagaa tgtgatttcc aagacaatca atccacaagt gtctaagact     180
gaatacaaag aacttcttca agagttcata gacgacaatg ccactacaaa tgccatagat     240
gaattgaagg aatgttttct taaccaaacg gatgaaactc tgagcaatgt tgaggtgttt     300
atgcaattaa tatatgacag cagtctttgt gatttatttt aactttctgc aagacctttg     360
gctcacagaa ctgcagggta tggtgagaaa ccaactacgg attgctgcaa accacacctt     420
ctctttctta tgtcttttta ctacaaacta caagacaatt gttgaaacct gctatacatg     480
tttattttaa taaattgatg gca                                             503
```

<210> SEQ ID NO 2
<211> LENGTH: 93
<212> TYPE: PRT
<213> ORGANISM: Homo sapiens

<400> SEQUENCE: 2

```
Met Lys Leu Leu Met Val Leu Met Leu Ala Ala Leu Ser Gln His Cys
 1               5                  10                  15
```

```
Tyr Ala Gly Ser Gly Cys Pro Leu Leu Glu Asn Val Ile Ser Lys Thr
             20                  25                  30

Ile Asn Pro Gln Val Ser Lys Thr Glu Tyr Lys Glu Leu Leu Gln Glu
         35                  40                  45

Phe Ile Asp Asp Asn Ala Thr Thr Asn Ala Ile Asp Glu Leu Lys Glu
     50                  55                  60

Cys Phe Leu Asn Gln Thr Asp Glu Thr Leu Ser Asn Val Glu Val Phe
 65                  70                  75                  80

Met Gln Leu Ile Tyr Asp Ser Ser Leu Cys Asp Leu Phe
                 85                  90

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:Synthetic

<400> SEQUENCE: 3
cagcggcttc cttgatcctt g                                          21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 4
ataagaaaga gaaggtgtgg                                            20

<210> SEQ ID NO 5
<211> LENGTH: 403
<212> TYPE: DNA
<213> ORGANISM: Homo sapiens

<400> SEQUENCE: 5
gacagcggct tccttgatcc ttgccacccg cgactgaaca ccgacagcag cagcctcacc    60
atgaagttgc tgatggtcct catgctggcg cccctctccc agcactgcta cgcaggctct   120
ggctgcccct tattggagaa tgtgatttcc aagacaatca atccacaagt gtctaagact   180
gaatacaaag aacttcttca agagttcata gacgacaatg ccactacaaa tgccatagat   240
gaattgaagg aatgttttct taaccaaacg gatgaaactc tgagcaatgt tgaggtgttt   300
atgcaattaa tatatgacag cagtctttgt gatttatttt aactttctgc aagacctttg   360
gctcacagaa ctgcagggta tggtgagaaa ccaactacgg att                    403

<210> SEQ ID NO 6
<211> LENGTH: 206
<212> TYPE: DNA
<213> ORGANISM: Homo sapiens

<400> SEQUENCE: 6
tttatgcaat taatatatga cagcagtctt tgtgatttat tttaactttc tgcaagacct    60
ttggctcaca gaactgcagg gtatggtgag aaaccaacta cggattgctg caaaccacac   120
cttctctttc ttatgtcttt ttactacaaa ctacaagaca attgttgaaa cctgctatac   180
atgtttattt taataaattg atggca                                       206

<210> SEQ ID NO 7
```

```
<211> LENGTH: 95
<212> TYPE: PRT
<213> ORGANISM: Homo sapiens

<400> SEQUENCE: 7

Met Lys Leu Val Phe Leu Phe Leu Leu Val Thr Ile Pro Ile Cys Cys
 1               5                  10                  15

Tyr Ala Ser Gly Ser Gly Cys Ser Ile Leu Asp Glu Val Ile Arg Gly
                20                  25                  30

Thr Ile Asn Ser Thr Val Thr Leu His Asp Tyr Met Lys Leu Val Lys
            35                  40                  45

Pro Tyr Val Gln Asp His Phe Thr Glu Lys Ala Val Lys Gln Phe Lys
        50                  55                  60

Gln Cys Phe Leu Asp Gln Thr Asp Lys Thr Leu Glu Asn Val Gly Val
 65                 70                  75                  80

Met Met Glu Ala Ile Phe Asn Ser Glu Ser Cys Gln Gln Pro Ser
                85                  90                  95

<210> SEQ ID NO 8
<211> LENGTH: 91
<212> TYPE: PRT
<213> ORGANISM: Homo sapiens

<400> SEQUENCE: 8

Met Lys Leu Ala Val Thr Leu Thr Leu Val Thr Leu Ala Leu Cys Cys
 1               5                  10                  15

Ser Ser Ala Ser Ala Glu Ile Cys Pro Ser Phe Gln Arg Val Ile Glu
                20                  25                  30

Thr Leu Leu Met Asp Thr Pro Ser Ser Tyr Glu Ala Ala Met Glu Leu
            35                  40                  45

Phe Ser Pro Asp Gln Asp Met Arg Glu Ala Gly Ala Gln Leu Lys Lys
        50                  55                  60

Leu Val Asp Thr Leu Pro Gln Lys Pro Arg Glu Ser Ile Ile Lys Leu
 65                 70                  75                  80

Met Glu Lys Ile Ala Gln Ser Ser Leu Cys Asn
                85                  90

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence:Synthetic

<400> SEQUENCE: 9
cacgaattca ctatcgattc tggaaccttc agagg                               35

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence:Synthetic

<400> SEQUENCE: 10
ctggttcggc ccacctctga aggttccaga atcgatag                            38

<210> SEQ ID NO 11
<211> LENGTH: 22
<212> TYPE: DNA
<213> ORGANISM: Artificial Sequence
```

-continued

```
<220> FEATURE:
<223> OTHER INFORMATION: Description of Artificial Sequence:Synthetic

<400> SEQUENCE: 11
aatccgtagt tggtttctca cc                                              22

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 12
ctttctgcaa gacctttggc                                                 20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:Synthetic

<400> SEQUENCE: 13
tttttttttt tttttttttt t                                               21

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence:Synthetic

<400> SEQUENCE: 14

Glu Val Phe Met Gln Leu Ile Tyr Asp Ser Ser Leu Cys Asp Leu Phe
 1               5                  10                  15

<210> SEQ ID NO 15
<211> LENGTH: 279
<212> TYPE: DNA
<213> ORGANISM: Homo sapiens

<400> SEQUENCE: 15
atgaagttgc tgatggtcct catgctggcg gccctctccc agcactgcta cgcaggctct     60
ggctgcccct tattggagaa tgtgatttcc aagacaatca atccacaagt gtctaagact    120
gaatacaaag aacttcttca agagttcata gacgacaatg ccactacaaa tgccatagat    180
gaattgaagg aatgttttct taaccaaacg gatgaaactc tgagcaatgt tgaggtgttt    240
atgcaattaa tatatgacag cagtctttgt gatttattt                           279

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 16
agcactgcta cgcaggctct                                                 20

<210> SEQ ID NO 17
<211> LENGTH: 74
<212> TYPE: PRT
<213> ORGANISM: Homo sapiens
```

```
-continued

<400> SEQUENCE: 17

Ser Gly Cys Pro Leu Leu Glu Asn Val Ile Ser Lys Thr Ile Asn Pro
 1               5                  10                  15

Gln Val Ser Lys Thr Glu Tyr Lys Glu Leu Leu Gln Glu Phe Ile Asp
            20                  25                  30

Asp Asn Ala Thr Thr Asn Ala Ile Asp Glu Leu Lys Glu Cys Phe Leu
        35                  40                  45

Asn Gln Thr Asp Glu Thr Leu Ser Asn Val Glu Val Phe Met Gln Leu
    50                  55                  60

Ile Tyr Asp Ser Ser Leu Cys Asp Leu Phe
 65                  70

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence:Synthetic

<400> SEQUENCE: 18
cgcggatcca ggattgtcct gcagat                                          26

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence:Synthetic

<400> SEQUENCE: 19
ccggaattcc catccctcta cccaga                                          26

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence:Synthetic

<400> SEQUENCE: 20
ccacccatgg caaattccat ggca                                            24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence:Synthetic

<400> SEQUENCE: 21
tctagacggc aggtcaggtc cacc                                            24
```